(12) United States Patent
Kanzaki

(10) Patent No.: US 7,452,487 B2
(45) Date of Patent: Nov. 18, 2008

(54) PHOSPHORUS-ACID-GROUP-CONTAINING (METH) ACRYLAMIDE, ITS POLYMER AND USE THEREOF, AND THEIR PRODUCTION METHODS

(75) Inventor: Yoshio Kanzaki, Nara-ken (JP)

(73) Assignee: Uni-Chemical Co., Ltd., Nara-Ken (JP)

( * ) Notice: Subject to any disclaimer, the term of this patent is extended or adjusted under 35 U.S.C. 154(b) by 51 days.

(21) Appl. No.: 10/590,569

(22) PCT Filed: Feb. 23, 2005

(86) PCT No.: PCT/JP2005/002939

§ 371 (c)(1),
(2), (4) Date: Aug. 24, 2006

(87) PCT Pub. No.: WO2005/080454

PCT Pub. Date: Sep. 1, 2005

(65) Prior Publication Data

US 2007/0173549 A1    Jul. 26, 2007

(30) Foreign Application Priority Data

Feb. 24, 2004   (JP) .............................. 2004-048818

(51) Int. Cl.
*H01B 1/00* (2006.01)
(52) U.S. Cl. .................. 252/500; 205/637; 252/180; 430/270.15; 526/278; 544/244; 558/145; 562/15; 564/204
(58) Field of Classification Search ................ 210/727; 252/500, 180; 523/118; 205/637; 430/270.15; 526/278; 544/244; 558/145; 562/15; 564/204
See application file for complete search history.

(56) References Cited

U.S. PATENT DOCUMENTS

| | | | | |
|---|---|---|---|---|
| 3,351,617 | A | * 11/1967 | Jaeger et al. | ................. 526/278 |
| 3,823,124 | A | * 7/1974 | Chang et al. | ................. 526/278 |
| 3,909,228 | A | * 9/1975 | Nakasima et al. | ................. 71/1 |
| 4,526,728 | A | * 7/1985 | Finke et al. | .................... 562/15 |
| 4,797,185 | A | * 1/1989 | Polak et al. | ................. 205/637 |
| 4,874,588 | A | * 10/1989 | Sortwell et al. | ............. 422/269 |
| 4,921,992 | A | * 5/1990 | Adams et al. | ............... 558/145 |
| 4,957,854 | A | * 9/1990 | Oguchi et al. | .......... 430/270.15 |
| 5,145,902 | A | * 9/1992 | Ravet et al. | ................. 524/425 |

(Continued)

FOREIGN PATENT DOCUMENTS

GB       1380675    *   1/1975

(Continued)

OTHER PUBLICATIONS

Kato et al., "Lysozyme loading in phosphate-bearing hydrogels at high density and the controller release of lysozyme," Dep. Chem. Sci. and Eng. Fac. Eng., 55(6), 1998, pp. 353-358.*

*Primary Examiner*—Douglas McGinty
*Assistant Examiner*—Khanh Tuan Nguyen
(74) *Attorney, Agent, or Firm*—Browdy and Neimark, P.L.L.C.

(57) ABSTRACT

A phosphorus-acid-group-containing (meth)acrylamide polymer having high electrolytic group density and excellent conductivity is obtained by introducing a phosphorus acid group into a (meth)acrylamide monomer which may be N-substituted, and polymerizing the resultant monomer. This polymer is usable for conductive resins, proton-conductive polymer electrolyte membranes and coating agents.

18 Claims, 2 Drawing Sheets

U.S. PATENT DOCUMENTS

| | | | | |
|---|---|---|---|---|
| 5,342,539 A | * | 8/1994 | Nagan | 252/180 |
| 5,393,436 A | * | 2/1995 | Nagan | 210/277 |
| 5,583,100 A | * | 12/1996 | Okamoto et al. | 508/441 |
| 6,452,004 B1 | * | 9/2002 | Katagiri et al. | 544/244 |
| 2004/0266906 A1 | * | 12/2004 | Klee et al. | 523/118 |

FOREIGN PATENT DOCUMENTS

| | | | |
|---|---|---|---|
| JP | 55-025473 | * | 2/1980 |
| JP | 07-019776 | * | 1/1995 |
| JP | 09-087510 | * | 3/1997 |
| JP | 09-324391 | * | 12/1997 |
| JP | 10-101661 | * | 4/1998 |
| JP | 10-251990 | | 9/1998 |
| JP | 2001-114834 | * | 4/2001 |
| JP | 2002-083514 | * | 3/2002 |
| JP | 2002-194013 | * | 7/2002 |
| JP | 2003-020308 | | 1/2003 |
| JP | 2003-022823 | | 1/2003 |
| JP | 2003-257238 | | 9/2003 |
| JP | 2004-331810 | | 11/2004 |
| WO | WO-02/33709 A1 | | 4/2002 |
| WO | WO 03/035013 A1 | * | 5/2003 |
| WO | WO-03/035013 A1 | | 5/2003 |

* cited by examiner

PHOSPHORUS-ACID-GROUP-CONTAINING (METH) ACRYLAMIDE, ITS POLYMER AND USE THEREOF, AND THEIR PRODUCTION METHODS

FIELD OF THE INVENTION

The present invention relates to phosphorus-acid-group-containing (meth)acrylamide useful as a starting material for conductive resins, polymer electrolyte membranes, etc., its polymer and use thereof, and their production methods.

BACKGROUND OF THE INVENTION

Acrylamide polymers having electrolytic groups such as phosphorus acid groups (for instance, a (poly)phosphoric group, a (poly)phosphonic group), or a sulfonate group are useful for wide varieties of applications as conductive materials, paper modifiers, hygiene materials, agricultural materials, etc. Among them, acrylamide polymers having phosphorus acid groups as electrolytic groups are insoluble in water and have excellent oxidation resistance and flame retardance despite hydrophilicity. Accordingly, they are useful particularly for various applications such as conductive resins, antistatic agents, paper modifiers and coating agents. For instance, JP10-251990A discloses a paper-making additive comprising phosphoric-group-containing poly(meth)acrylamide derivatives.

However, when electrolytic-group-containing acrylamide polymers are used as solid polymer electrolytes, they are desired to have higher conductivity. To improve the conductivity of the electrolytic-group-containing acrylamide polymers, it is effective to increase their electrolytic group densities, for instance. However, the phosphoric-group-containing poly(meth)acrylamide derivatives of JP10-251990A, which are obtained by copolymerizing(meth)acrylamide and phosphoric-group-containing, unsaturated monomers, fail to have a satisfactory level of electrolytic group densities.

Thus, the applicant proposed a sulfonate-group-containing acrylamide polymer obtained by introducing a (poly)phosphonic group into a polymer constituted by a unit represented by the following general formula (21):

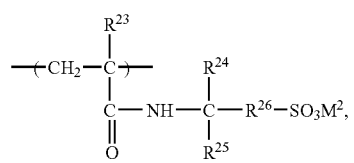

wherein $R^{23}$ is a hydrogen group or a methyl group, $R^{24}$ and $R^{25}$ are a hydrogen group or an alkyl group having 1-3 carbon atoms, $R^{26}$ is an alkylene group having 1-3 carbon atoms, $M^2$ is a hydrogen group, an alkali metal, an ammonium ion or an amine group (JP2004-331810A). However, this polymer differs from those obtained by introducing a phosphorus acid group into sulfonate-group-containing (meth)acrylamide monomers, and polymerizing the resultant derivatives. Accordingly, the polymer of JP2004-331810A fails to have a satisfactory level of electrolytic group density.

OBJECT OF THE INVENTION

Accordingly, an object of the present invention is to provide phosphorus-acid-group-containing (meth)acrylamide for producing an acrylamide polymer having a high electrolytic group density, and its polymer and application, and methods for producing them.

DISCLOSURE OF THE INVENTION

As a result of intensive research in view of the above object, the inventor has found that a polymer having a high electrolytic group density and thus excellent conductivity is obtained by introducing a phosphorus acid group into a (meth)acrylamide monomer, which may be N-substituted, and polymerizing the resultant monomer. The inventor has also found that the phosphorus acid group can easily be introduced into the (meth)acrylamide monomer, which may be N-substituted, by (a) reacting the (meth)acrylamide monomer with phosphoric anhydride and/or phosphorus oxychloride, and hydrolyzing the resultant product, or (b) reacting the (meth)acrylamide monomer with at least one selected from the group consisting of phosphoric acid, pyrophosphoric acid and polyphosphoric acid. The present invention has been completed based on these findings.

Thus, the phosphorus-acid-group-containing (meth)acrylamide of the present invention is obtained by introducing a phosphorus acid group into a (meth)acrylamide monomer represented by the following formula (1):

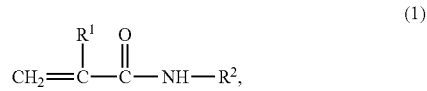

wherein $R^1$ is a hydrogen group or a methyl group, and $R^2$ is a hydrogen group or a substituted or unsubstituted hydrocarbon group.

The phosphorus acid group is preferably added to the amide group of the (meth)acrylamide monomer. The phosphorus acid group is preferably a phosphonic group or a polyphosphonic group. The (meth)acrylamide monomer is preferably at least one selected from the group consisting of acrylamide, methacrylamide, and acrylamide alkane sulfonate represented by the following formula (2):

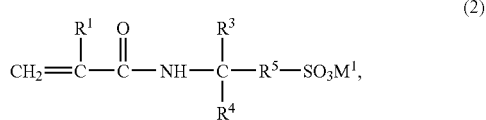

wherein $R^1$ is a hydrogen group or a methyl group, $R^3$ and $R^4$ are a hydrogen group or an alkyl group having 1-3 carbon atoms, $R^5$ is an alkylene group having 1-3 carbon atoms, and $M^1$ is a hydrogen group, a metal or a tertiary-amine group.

The acrylamide alkane sulfonate is preferably t-butyl acrylamide sulfonic acid represented by the following formula (3):

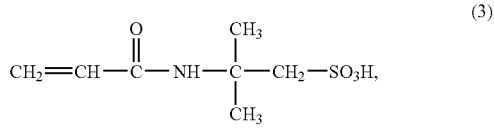

The phosphorus-acid-group-containing (meth)acrylamide polymer of the present invention is obtained by polymerizing at least the above phosphorus-acid-group-containing (meth)acrylamide. This polymer may contain another unsaturated compound as a comonomer, which is preferably (a) an unsaturated compound containing one or more ethylenically unsaturated bonds and one or more acid groups in a molecule, and/or (b) an unsaturated compound containing one or more ethylenically unsaturated bonds but no acid group in a molecule.

The acid-group-containing, unsaturated compound (a) preferably has at least one acid group selected from the group consisting of a phosphoric group, a sulfonic group, a carboxylic group and an alcoholic hydroxyl group. The alcoholic-hydroxyl-group-containing, unsaturated compound is preferably phosphatized. The unsaturated compound with no acid group (b) is preferably at least one selected from the group consisting of (meth)acrylonitrile, (meth)acrylamide, (meth)acrylate, alkyl-amino-group-containing, unsaturated monomers, liquid oligomers of conjugated dienes and their derivatives, liquid oligomers of vinyl aromatics and conjugated dienes and their derivatives, substituted or unsubstituted styrenes, vinyl halides, aliphatic acid vinyl esters, and fluoro-group-containing, unsaturated monomers. These other unsaturated compounds may be cross-linking agents having two or more ethylenically unsaturated bonds in a molecule.

The alkyl-amino-group-containing, unsaturated monomer is preferably an N,N-dialkyl (meth)acrylamide represented by the following formula (4):

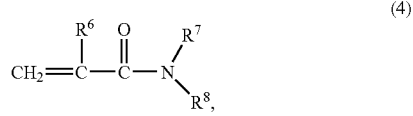

(4)

wherein $R^6$ is a hydrogen group or a methyl group, and $R^7$ and $R^8$ are independently alkyl groups.

The conductive resin of the present invention comprises the above phosphorus-acid-group-containing (meth)acrylamide polymer as an indispensable component. The conductive resin may comprise at least one selected from the group consisting of unsaturated alcohol copolymers comprising an unsaturated alcohol unit and a vinyl halide unit and/or an aliphatic acid vinyl ester unit, partially acetalized unsaturated alcohol polymers, melamine resins, poly(meth)acrylonitrile, poly(meth)acrylate, polyacrylamide, poly(meth)acrylic acid, polyacetal, urethane resins, cellulose or its modified products, polystyrene, polyvinyl chloride, and polyvinyl acetate.

The coating agent of the present invention is a solution comprising the above conductive resin.

The polymer electrolyte membrane of the present invention comprises the above conductive resin as a solid polymer electrolyte and has proton conductivity. The polymer electrolyte membrane of the present invention is suitable for fuel cells.

The method of the present invention for producing a phosphorus-acid-group-containing (meth)acrylamide comprises (a) reacting a (meth)acrylamide monomer represented by the above formula (1) with phosphoric anhydride and/or phosphorus oxychloride, and hydrolyzing the resultant product, or (b) reacting a (meth)acrylamide monomer with at least one selected from the group consisting of phosphoric acid, pyrophosphoric acid and polyphosphoric acid, in a solvent containing no active hydrogen and/or an acidic solvent.

The solvent containing no active hydrogen is preferably at least one selected from the group consisting of N,N-dialkyl (meth)acrylamide represented by the above formula (4), dimethylformamide, N,N-dimethylacetamide, and dimethyl sulfoxide. The N,N-dialkyl(meth)acrylamide is preferably N,N-dimethyl(meth)acrylamide.

The method of the present invention for producing a phosphorus-acid-group-containing (meth)acrylamide polymer comprises polymerizing at least the phosphorus-acid-group-containing (meth)acrylamide prepared by the above method. The phosphorus-acid-group-containing (meth)acrylamide may be prepared using N,N-dialkyl(meth)acrylamide represented by the above formula (4) as a solvent containing no active hydrogen, and the N,N-dialkyl(meth)acrylamide and the phosphorus-acid-group-containing (meth)acrylamide may be copolymerized using the resultant reaction solution. A composition comprising at least the phosphorus-acid-group-containing (meth)acrylamide obtained by the above production method and a release agent may be prepared, and the resultant composition may be radiation-polymerized in a state where it is sandwiched by two supporting substrates. The radiations are preferably ultraviolet rays, X-rays or electron beams. When ultraviolet rays are used, a photopolymerization initiator is added to the above composition.

Figure 1:
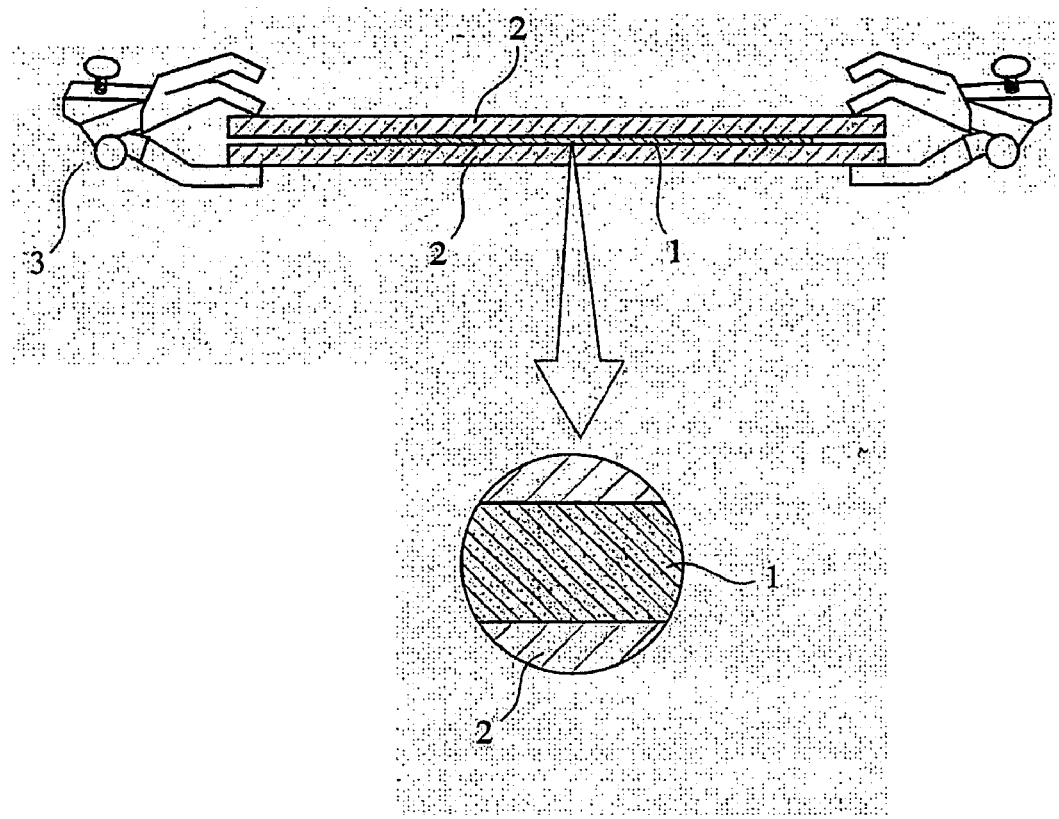
FIG. 1 is a partially cross-sectional side view showing an unsaturated composition sandwiched by two flat glass plates.

1 Unsaturated composition,
2 Flat glass plate,
3 Clip,
4 Softness tester,
40 Upper surface,
41 Lower surface,
42 Slanting surface, and
43 Scale.

DESCRIPTION OF THE BEST MODE OF THE INVENTION

[1] (Meth)acrylamide Monomer

A (meth)acrylamide monomer, a starting material for the phosphorus-acid-group-containing (meth)acrylamide of the present invention, is represented by the following formula (1):

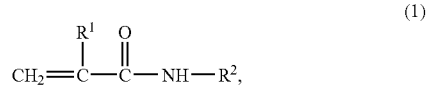

(1)

wherein $R^1$ is a hydrogen group or a methyl group, and $R^2$ is a hydrogen group or a substituted or unsubstituted hydrocarbon group.

$R^1$ in the formula (1) is preferably a hydrogen group to improve polymerizability. $R^2$ is preferably a hydrogen group to introduce phosphorus-acid-groups, and to improve an electrolytic group density in the resultant polymer. When $R^2$ is a hydrocarbon group, it may be, for instance, an alkyl group such as a methyl group, an ethyl group, an n-propyl group, an isopropyl group, an n-butyl group, an isobutyl group, a sec-butyl group, a tert-butyl group, a 2-methyl butyl group, a 3-methyl butyl group, an n-octyl group, a 2-ethylhexyl group, etc.; a cycloalkyl group such as a cyclopropyl group, a cyclohexyl group, etc.; an aryl group such as a phenyl group, etc. These hydrocarbon groups may be substituted, and examples of the substituent group may be a sulfonic group which may form complexes; an alkoxyl methyl group such as a methoxymethyl group, an ethoxymethyl group, an n-propoxymethyl group, an isopropoxymethyl group, a tert-butoxymethyl group, etc.; an amino group such as an N,N-dimethyl amino group, an N,N-diethyl amino group, etc. Among them, the substituted hydrocarbon groups are preferably those having a sulfonic group, which may form complexes, to improve an electrolytic group density when polymers are prepared.

The (meth)acrylamide monomer is preferably at least one selected from the group consisting of acrylamide, methacrylamide, and acrylamide alkane sulfonate represented by the following formula (2):

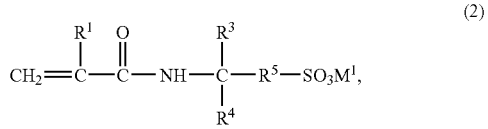

wherein $R^1$ is a hydrogen group or a methyl group, $R^3$ and $R^4$ are a hydrogen group or an alkyl group having 1-3 carbon atoms, $R^5$ is an alkylene group having 1-3 carbon atoms, and $M^1$ is a hydrogen group, a metal or a tertiary-amine group.

The acrylamide alkane sulfonate is preferably t-butyl acrylamide sulfonic acid represented by the following formula (3):

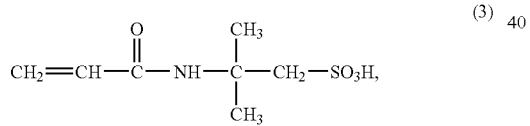

[2] Production Method of Phosphorus-acid-group-containing (meth)acrylamide

The phosphorus-acid-group-containing (meth)acrylamide of the present invention is obtained by (a) reacting the above (meth)acrylamide monomer with phosphoric anhydride (phosphorus pentoxide $P_2O_5$) and/or phosphorus oxychloride, and hydrolyzing the resultant product, or (b) reacting the above (meth)acrylamide monomer with at least one selected from the group consisting of phosphoric acid, pyrophosphoric acid and polyphosphoric acid. Accordingly, the phosphorus acid group introduced into the (meth)acrylamide monomer are derived from at least one phosphorus acid selected from the group consisting of phosphoric anhydride, phosphorus oxychloride, phosphoric acid, pyrophosphoric acid and polyphosphoric acid. Among them, the phosphorus acid is preferably phosphoric anhydride. Phosphoric anhydride has such high reactivity that the phosphorus acid group can be smoothly introduced into the (meth)acrylamide monomer. Detailed explanations will be made below with respect to the production method of phosphorus-acid-group-containing (meth)acrylamide using phosphoric anhydride as phosphorus acid.

When the (meth)acrylamide monomer is reacted with phosphoric anhydride, as shown in the following formula (5):

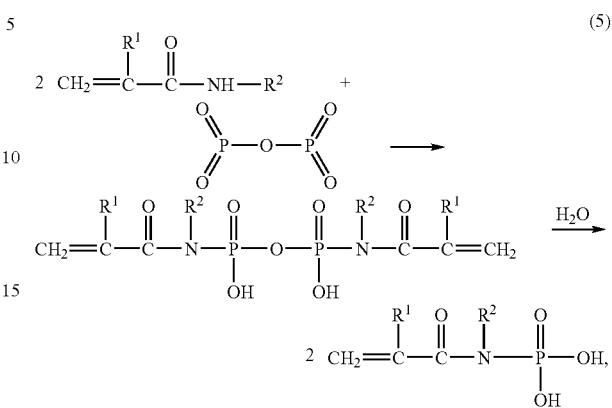

wherein $R^1$ and $R^2$ are the same as in the formula (1), pyrophosphonic diacrylamide is presumably formed as an intermediate product and hydrolyzed, so that (meth)acrylamide monomer having a phosphonic group added thereto is formed. A molar ratio of phosphoric anhydride to the (meth)acrylamide monomer is preferably 0.5-0.8, more preferably 0.5-0.6, particularly 0.52-0.58. To achieve full hydrolysis, water is added at a molar ratio of preferably 0.5-0.8, more preferably 0.5-0.6, to the (meth)acrylamide monomer. The hydrolysis is preferably conducted after all phosphoric anhydride is added, so that the phosphorus acid group is smoothly added to the amide group. It should be noted, however, that the hydrolysis need not necessarily be conducted after all phosphoric anhydride is added, but water may be added simultaneously with phosphoric anhydride, if necessary.

When the molar ratio of phosphoric anhydride to the (meth)acrylamide monomer is more than 0.5, a compound represented by the following formula (6):

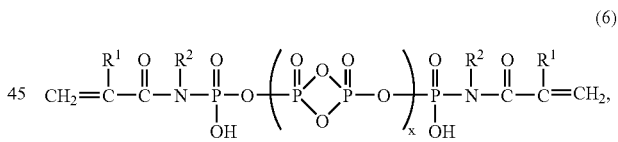

wherein $R^1$ and $R^2$ are the same as in the formula (1), and x is 1 or 2, is also presumably formed as an intermediate product. The phosphorus-acid-group-containing (meth)acrylamide, which is formed by the hydrolysis of the compound represented by the formula (6), may contain a polyphosphonic-group-containing monomer represented by the following formula (7):

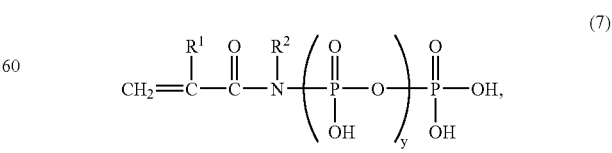

wherein $R^1$ and $R^2$ are the same as in the formula (1), and y is 1 or 2.

Formed when acrylamide and/or methacrylamide as the (meth)acrylamide monomer are reacted with phosphoric anhydride are not only monomers having only one phosphonic or polyphosphonic group added, but also for instance, as shown by reactions represented by the following formula (8):

polyphosphoric acid, etc. are precipitated by cooling, precipitated solid is separated by suction filtration. Water is added to the resultant reaction solution. This causes heat generation, and hydrolysis is conducted at a temperature of 60-100° C. for 15 minutes to 1 hour.

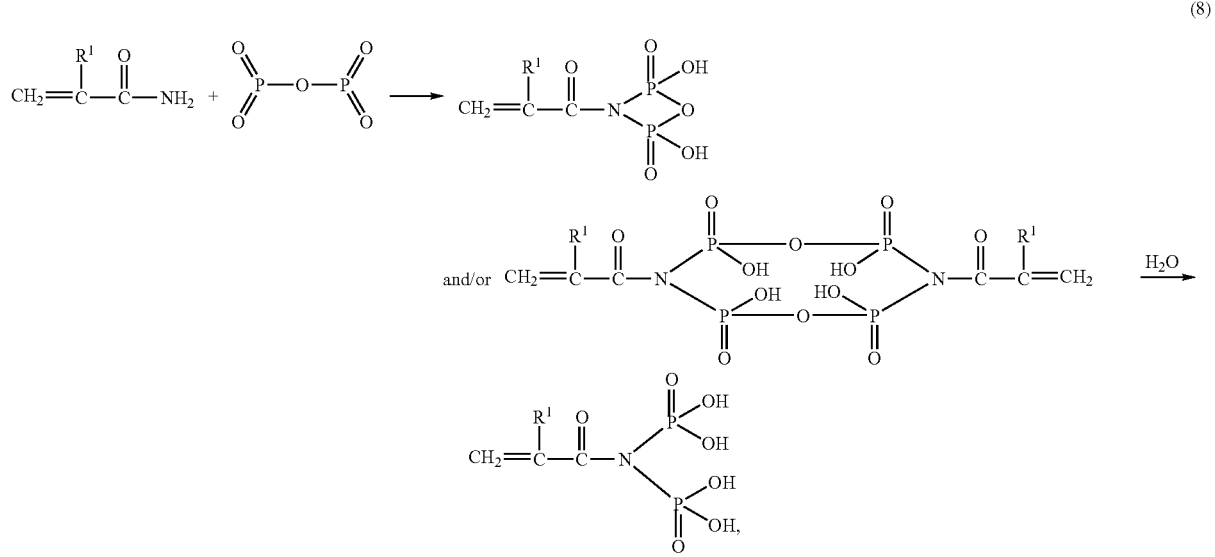

(8)

wherein $R^1$ is a hydrogen group or a methyl group, N,N-diphosphonic(meth)acrylamide is presumably formed through a compound having pyrophosphoric acid N,N-linked to (meth)acrylamide and/or a compound having two (meth) acrylamide molecules bonded via dipyrophosphoric acid, as an intermediate product.

Accordingly, when phosphonic (meth)acrylamide is mainly produced using acrylamide and/or methacrylamide, the molar ratio of phosphoric anhydride to (meth)acrylamide is preferably 0.5-0.8, more preferably 0.5-0.6, particularly 0.52-0.58. When N,N-diphosphonic (meth)acrylamide is mainly produced using acrylamide and/or methacrylamide, the molar ratio of phosphoric anhydride to (meth)acrylamide is preferably 1-1.2, more preferably 1-1.15, particularly 1.05-1.15. When N,N-diphosphonic (meth)acrylamide is mainly produced, the molar ratio of water to (meth)acrylamide is preferably 1-1.3 in the hydrolysis.

Reaction procedures in the case of using phosphoric anhydride will be explained below. A solution comprising a (meth) acrylamide monomer and a solvent is first charged into a reactor equipped with a stirrer and a reflux condenser, and heated to 50-75° C. At this time, it is preferable to add a known polymerization inhibitor such as hydroquinone monomethyl ether, paramethoxyhydroquinone, etc. together. After reaching a predetermined temperature, phosphoric anhydride is added. Phosphoric anhydride is preferably added with 2-10 installments over 1-7 hours, to accelerate the reaction of forming a (poly)phosphonic-group-containing acrylamide monomer with improved yields, though not intending to restrict thereto. The addition of phosphoric anhydride causes heat generation, so that the reaction temperature is usually elevated to about 70-90° C. Thereafter, it is kept at 50-110° C. to continue the reaction for 1-3 hours. The resultant reaction solution is cooled to room temperature. When the unreacted phosphoric anhydride, the by-produced inorganic The solvent used is preferably a solvent containing no active hydrogen and/or an acidic solvent. The solvents containing no active hydrogen include amide solvents such as N,N-dialkyl(meth)acrylamide represented by the following formula (4):

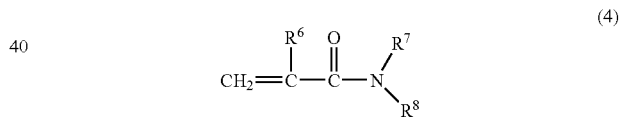

(4)

wherein $R^6$ is a hydrogen group or a methyl group, and $R^7$ and $R^8$ are independently alkyl groups, dimethylformamide (DMF), N,N-dimethylacetamide (DMAc), etc.; and sulfoxide solvents such as dimethyl sulfoxide (DMSO), etc. The acidic solvents include organic acid solvents such as alkyl carboxylic acids, alkyl phosphoric acids, etc. These solvents may be used alone or in combination.

Among these solvents, at least one selected from the group consisting of N,N-dialkyl(meth)acrylamide, DMF, DMAc and DMSO is preferable. Among the N,N-dialkyl(meth)acrylamide, N,N-dimethyl acrylamide (DMAA) is advantageous in that it has excellent solubility for a (meth)acrylamide monomer, phosphoric anhydride and (poly)phosphonic-group-containing (meth)acrylamide, that it can select a wide range of reaction temperatures because of a boiling point of 171-172° C., that it can fully prevent side reactions by using a polymerization inhibitor, and so on.

To accelerate the reaction and suppress the formation of by-products, the reaction solution has an initial concentration before adding phosphoric anhydride [concentration of (meth) acrylamide monomer] of preferably 20-70% by mass, more preferably 25-60% by mass.

When (poly)phosphonic-group-containing (meth)acrylamide is isolated after the reaction, the reaction solution is trickled into a poor solvent to deposit and filter out a viscous paste-like liquid. The poor solvent is preferably a non-polar solvent, for instance, acetone, tetrahydrofuran (THF), dioxane, benzene, toluene, xylene, ether, etc. The non-polar solvent preferably has a small specific gravity and a relatively low boiling point. The poor solvent is used in such excess amount as 5-15 times by volume the reaction product. The washing operation of the viscous liquid with the poor solvent may be repeated if necessary. The isolated (poly)phosphonic-group-containing (meth)acrylamide is dried. The drying method is preferably evacuation at temperatures from room temperature to 100° C., heating at 60-100° C. for 1-4 hours using a hot-air oven, etc.

[3] Phosphorus-acid-group-containing (Meth)acrylamide

The phosphorus-acid-group-containing (meth)acrylamide obtained by the above production method presumably has a general structure comprising a (poly)phosphonic group represented by the following formula (9):

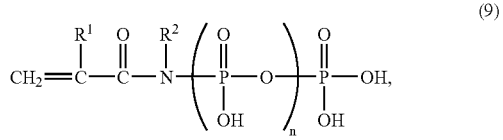

(9)

wherein $R^1$ and $R^2$ are the same as in the formula (1), and n is an integer of 0-2.

Among them, the phosphorus-acid-group-containing (meth)acrylamide presumably contains as a main component a compound comprising a phosphonic group represented by the following formula (10):

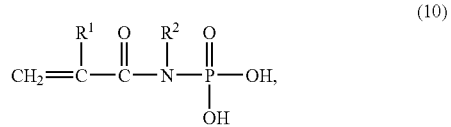

(10)

wherein $R^1$ and $R^2$ are the same as in the formula (1).

When acrylamide and/or methacrylamide is used as the (meth)acrylamide monomer as described above, not only (poly)phosphonic(meth)acrylamide, but also N,N-diphosphonic (meth)acrylamide represented by the following formula (11):

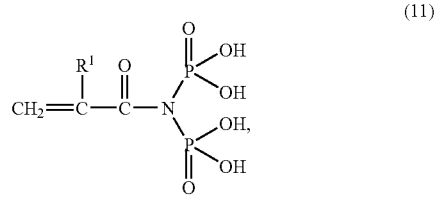

(11)

wherein $R^1$ is a hydrogen group or a methyl, are presumably formed. With the molar ratio of phosphoric anhydride to (meth)acrylamide being about 1 or more, N,N-diphosphonic (meth)acrylamide presumably becomes a main component.

A phosphorus acid group (a phosphonic group, a (poly) phosphonic group, etc.) in the phosphorus-acid-group-containing (meth)acrylamide may form complexes, to further improve, for instance, hydrolysis resistance, heat resistance, etc. The complexes are preferably ammonium salts, amine salts or metal salts. In the case of forming ammonium salts or amine salts, to neutralize acid, it is preferable to form complexes, for instance, with ammonium ions containing primary, secondary, tertiary or quaternary alkyl, allyl or aralkyl groups, or mono-, di- or tri-alkanol amine groups. The metal salts are preferably alkali metal salts such as potassium salts; and heavy metal salts such as cuprous oxide salts (red brown), cupric oxide salts (blue), equimolar mixtures (gray) of cuprous oxide/cupric oxide salts, ferric oxide salts (brown), etc. These complexes may be used alone or in combination.

[4] Phosphorus-acid-group-containing (Meth)acrylamide Polymer

The phosphorus-acid-group-containing (meth)acrylamide polymer of the present invention is obtained by polymerizing at least the above phosphorus-acid-group-containing (meth) acrylamide. This polymer may contain other unsaturated compounds copolymerizable with the phosphorus-acid-group-containing (meth)acrylamide.

(1) Other Copolymerizable Unsaturated Compounds

The other unsaturated compounds are classified to the following two groups: (a) unsaturated compounds containing one or more ethylenically unsaturated bonds and one or more acid groups in a molecule, and (b) unsaturated compounds containing one or more ethylenically unsaturated bonds but no acid group in a molecule.

(a) Acid-group-containing, Unsaturated Compounds

To improve conductivity, film-forming properties, chemical resistance, etc., the phosphorus-acid-group-containing (meth)acrylamide polymer preferably contains another acid-group-containing, unsaturated compound as a comonomer. The acid group is preferably at least one selected from the group consisting of a phosphoric group, a sulfonic group, a carboxylic group and an alcoholic hydroxyl group. The skeleton having ethylenically unsaturated bonds may be a (meth) acrylate skeleton, a (meth)allyl ester skeleton, etc.

(i) Phosphoric-group-containing, Unsaturated Monomer

Examples of the phosphoric-group-containing, unsaturated monomer are represented by the following general formula (12):

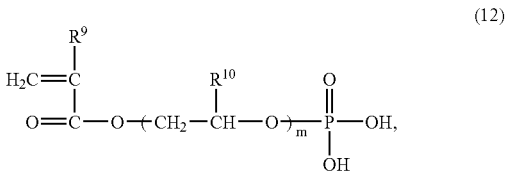

(12)

wherein $R^9$ is a hydrogen group or an alkyl group, $R^{10}$ is a hydrogen group or a substituted or unsubstituted alkyl group, and m is an integer of 1-6, which is called "monomer (I)" unless otherwise mentioned. $R^9$ is preferably H or $CH_3$, and $R^{10}$ is preferably H, $CH_3$ or $CH_2Cl$.

The structural formulae and properties of typical monomers (I) are shown in Tables 1 and 2. These monomers are commercially available from Uni-Chemical Co. Ltd. under the registered trademark of "Phosmer," though the phosphoric-group-containing, unsaturated monomers usable in the present invention are not restricted thereto.

TABLE 1

| Name | Structure Formula | Grade Name |
|---|---|---|
| Acid Phosphoxy Ethyl Methacrylate | $H_2C=C(CH_3)-C(=O)-O-CH_2-CH_2-O-P(=O)(OH)_2$ | Phosmer M |
| Salt of Methacroyl Oxyethyl Acid Phosphate and Monoethanolamine | $H_2C=C(CH_3)-C(=O)-O-CH_2-CH_2-O-P(=O)(OH)(O^-\ ^+NH_2-CH_2-CH_2-OH)$ | Phosmer MH |
| 3-Chloro-2-Acid Phosphoxy Propyl Methacrylate | $H_2C=C(CH_3)-C(=O)-O-CH_2-CH(CH_2Cl)-O-P(=O)(OH)_2$ | Phosmer CL |
| Acid Phosphoxy Polyoxyethylene Glycol Monomethacrylate | $H_2C=C(CH_3)-C(=O)-O-(CH_2-CH_2-O)_m-P(=O)(OH)_2$, $m = 4 \sim 6$ | Phosmer PE |
| Acid Phosphoxy Polyoxyethylene Glycol Monomethacrylate | $H_2C=C(CH_3)-C(=O)-O-(CH_2-CH(CH_3)-O)_m-P(=O)(OH)_2$, $m = 5 \sim 6$ | Phosmer PP |

TABLE 2

| | | Grade (Phosmer ®) | | | | |
|---|---|---|---|---|---|---|
| | | M | MH | CL | PE | PP |
| Molecular Weight (g)/ Phosphoric Acid Equivalent (g) | | 210 | 271 | 258.5 | 360 | 460 |
| Specific Gravity (at 20° C.) | | 1.392 | 1.302 | 1.453 | 1.248 | 1.157 |
| Refractive Index (nd at 20° C.) | | 1.4562 | 1.4815 | 1.4785 | 1.4696 | 1.4577 |
| Viscosity (poise at 20° C.)[1] | | 80 (No. 1) | 800 (No. 2) | 700 (No. 2) | 25 (No. 1) | 55 (No. 2) |
| Acid Value | Theoretical Value | 533.3 | 206.6 | 433.3 | — | — |
| | Measured Value | ≦500 | 196 | 410 | 311 | 244 |
| | pH | — | 9.4 | — | — | — |
| Water Solubility[2] | at 20° C. | 4.1 | 4.3 | 1.3 | — | — |
| | at 25° C. | — | — | — | 4.0 | 3.2 |
| Monomer-Soluble Solvent | | Organic Acids, Ketones, | 2-Hydroxyethyl Methacrylate, Methanol, Ethanol, | Organic Acids, Ketones, | Organic Acids, Ketones, | Benzene, Toluene, Xylene |

TABLE 2-continued

| | Grade (Phosmer ®) | | | |
|---|---|---|---|---|
| M | MH | CL | PE | PP |
| Alcohols | Isopropyl Alcohol, Acrylic Acid, Acetic Acid | Alcohols | Alcohols | |

Note:
[1]Measured by a Brookfield viscometer (number of a rotor).
[2]The unit is % by mass.

The phosphoric group in the monomer (I) may be dissociated or form a complex. In the case of a complex, to neutralize electric charge, it is formed with ammonium ions containing, for instance, a primary, secondary, tertiary or quaternary alkyl, allyl or aralkyl group, or mono-, di- or tri-alkanol amine group, particularly $N^+R^{11}_{4-f}(OH)_f$, wherein $R^{11}$ is at least one selected from the group consisting of alkyl groups having 1-18 carbon atoms, aromatic groups having 6-12 carbon atoms, and alicyclic groups having 6-12 carbon atoms, and f is a positive integer of 1-3.

The phosphoric-group-containing, unsaturated monomer may be a phosphoric-group-containing, unsaturated diester monomer represented by the following general formula (13):

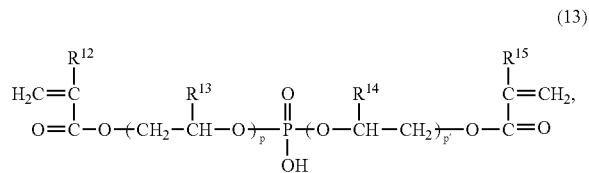

wherein $R^{12}$ and $R^{15}$ are independently a hydrogen group or a methyl group, $R^{13}$ and $R^{14}$ are independently a hydrogen group or a substituted or unsubstituted alkyl group, p and p' are independently an integer of 1-6, which is called "monomer (II)" unless otherwise mentioned.

The monomer (II) is preferably di(meth)acryloyloxyethyl phosphate represented by the following formula (14);

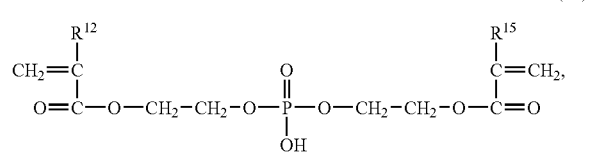

wherein $R^{12}$ and $R^{15}$ are independently a hydrogen group or a methyl. The monomer (II) may be used alone or in combination with the monomer (I) in the copolymerization.

(ii) Sulfonic-group-containing Unsaturated Monomer

The sulfonic-group-containing unsaturated monomer may be, for instance, the above t-butyl acrylamide sulfonic acid, allyl sulfonic acid, meta-allyl sulfonic acid, vinyl sulfonic acid, p-styrene sulfonic acid, (meth)acrylic acid butyl-4-sulfonic acid, (meth)acryloxy benzene sulfonic acid, etc. They may be used alone or in combination.

(iii) Carboxylic-group-containing Unsaturated Monomer

The carboxylic-group-containing unsaturated monomer may be (meth)acrylic acid, crotonic acid, maleic acid, fumaric acid, itaconic acid, maleic anhydride, etc. They may be used alone or in combination.

(iv) Alcoholic-hydroxyl-group-containing Unsaturated Monomer

The alcoholic-hydroxyl-group-containing unsaturated monomer may be glycerol di(meth)acrylate such as glycerol dimethacrylate (for instance, Blemmer GMR, Blemmer GMR-R and Blemmer GMR-H available from NOF Corp.), glycerol methacrylate acrylate (for instance, Blemmer GAM and Blemmer GAM-R available from NOF Corp.), etc.; 1,6-hexanediol diglycidyl ether acrylate (for instance, NK OLIGO EA-5521 available from Shin-Nakamura Chemical Co., Ltd.); 1,4-butanediol diglycidyl ether acrylate (for instance, NK OLIGO EA-5520 available from Shin-Nakamura Chemical Co., Ltd.); bisphenol A-type epoxy acrylate (for instance, NK OLIGO EA-1020 available from Shin-Nakamura Chemical Co., Ltd.); hexamethylenediol di(meth)acrylate; 2-hydroxy(meth)acrylate such as 2-hydroxy methyl (meth)acrylate, 2-hydroxy ethyl(meth)acrylate, etc.

Among them, glycerol di(meth)acrylate, 1,6-hexanediol diglycidyl ether acrylate, 1,4-butanediol diglycidyl ether acrylate, bisphenol A-type epoxy acrylate and hexamethylenediol diacrylate are preferable, because they are highly compatible with the phosphorus-acid-group-containing (meth)acrylamide, and have two ethylenically unsaturated groups in a molecule.

With their hydroxyl groups turned to phosphate groups, these alcoholic-hydroxyl-group-containing, unsaturated monomers have further improved compatibility with the phosphorus-acid-group-containing (meth)acrylamide. Particularly a monomer obtained by phosphatizing the alcoholic-hydroxyl-group-containing, unsaturated monomer having two ethylenically unsaturated groups in a molecule exhibits high cross-linkability in radiation polymerization. Preferable among such phosphatized monomers are compounds obtained by phosphatizing glycerol di(meth)acrylate, namely, a compound represented by the following formula (15):

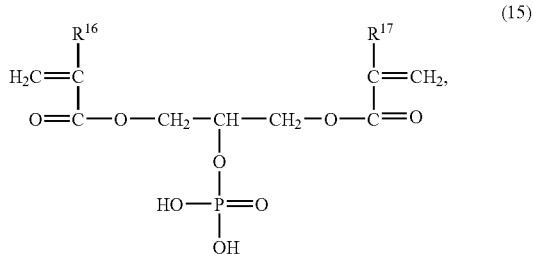

wherein $R^{16}$ and $R^{17}$ are independently a hydrogen group or a methyl group, and a compound represented by the following formula (16):

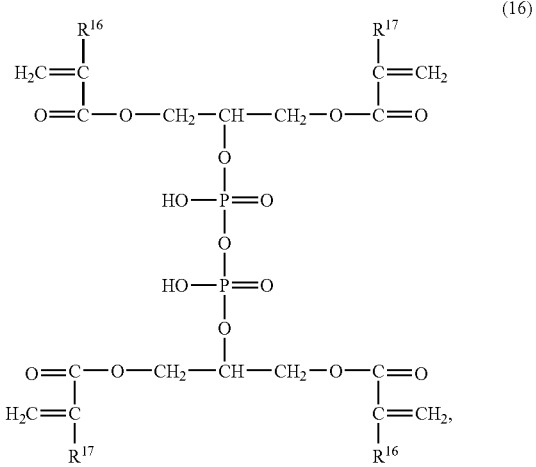

(16)

wherein $R^{16}$ and $R^{17}$ are independently a hydrogen group or a methyl group.

A method for phosphatizing the alcoholic-hydroxyl-group-containing, unsaturated monomer may be the same as the method for adding (poly)phosphonic acid to the above (meth)acrylamide monomer, except for using 0.5-0.6 mole equivalent of phosphoric anhydride per a hydroxyl group. However, when the compound represented by the above formula (16) is prepared, no hydrolysis is needed after adding phosphoric anhydride.

(v) Monomer Having an Acid Group and Pluralities of Ethylenically Unsaturated Bonds in a Molecule To improve the solvent resistance (for instance, methanol resistance, etc.) of the phosphorus-acid-group-containing (meth)acrylamide polymer, it is preferable to use an unsaturated compound having an acid group and pluralities of ethylenically unsaturated bonds to cross-link the phosphorus-acid-group-containing (meth)acrylamide polymer. Such cross-linking agents are preferably the phosphoric-group-containing, unsaturated diester monomers represented by the above formula (13), and glycerol di(meth)acrylate, 1,6-hexanediol diglycidyl ether acrylate, 1,4-butanediol diglycidyl ether acrylate, bisphenol A-type epoxy acrylate, hexamethylenediol diacrylate and their phosphatized products.

(b) Unsaturated Compound Containing No Acid Group

To improve film-forming properties, water resistance, chemical resistance, etc., the phosphorus-acid-group-containing (meth)acrylamide polymer may contain an unsaturated compound containing no acid group as a comonomer. The unsaturated compounds containing no acid group may be, in addition to those described in (a), any unsaturated compounds having one or more ethylenically unsaturated bonds in a molecule, which are not gaseous at room temperature. Preferable among them is at least one selected from the group consisting of (meth)acrylonitrile, (meth)acrylamide, (meth)acrylate, alkyl-amino-group-containing, unsaturated monomers, liquid oligomers of conjugated dienes and their derivatives, liquid oligomers of vinyl aromatics and conjugated dienes and their derivatives, substituted or unsubstituted styrenes, vinyl halides (for instance, vinyl chloride, etc.), aliphatic acid vinyl esters (for instance, vinyl acetate, etc.), and fluoro-group-containing, unsaturated monomers.

(i) (Meth)acrylate

The (meth)acrylate may be alkyl(meth)acrylate such as methyl(meth)acrylate, ethyl(meth)acrylate, etc.; urethane acrylate formed from diisocyanate and glycerol di(meth) acrylate (for instance, NK OLIGO U-4HA available from Shin-Nakamura Chemical Co., Ltd.); ethylene glycol di(meth)acrylate; trimethylolpropane tri(meth)acrylate, etc.

(ii) Alkyl-amino-group-containing, Unsaturated Monomers

The alkyl-amino-group-containing, unsaturated monomers may be the above N,N-dialkyl(meth)acrylamide, dimethyl amino ethyl(meth)acrylate, diethyl amino ethyl(meth) acrylate, dimethylaminopropyl(meth)acrylate, dimethyl amino butyl(meth)acrylate, dipropylaminoethyl(meth)acrylate, dibutylaminoethyl(meth)acrylate, dimethylaminoethyl (meth)acrylamide, diethylaminoethyl(meth)acrylamide, dimethylaminopropyl(meth)acrylamide, dimethylaminobutyl(meth)acrylamide, dipropylaminoethyl(meth)acrylamide, dibutylaminoethyl(meth)acrylamide, etc.

(iii) Liquid Oligomers of Conjugated Dienes

The liquid oligomer of conjugated diene is preferably at least one selected from the group consisting of butadiene oligomers having at least one ethylenically unsaturated bond in a molecule, isoprene oligomers, and their derivatives. The liquid oligomer of conjugated diene is more preferably represented by the following general formula (17):

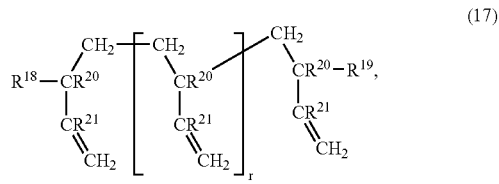

(17)

wherein $R^{18}$ and $R^{19}$ are independently (I) a hydrocarbon group having one or more ethylenically unsaturated bonds, which may have another atom group, (II) a hydrocarbon group having no ethylenically unsaturated bond, which may have another atom group, or (III) a hydrogen group, at least one of $R^{18}$ and $R^{19}$ being the above hydrocarbon group (I) having ethylenically unsaturated bonds; $R^{20}$ and $R^{21}$ are independently a hydrogen group or a methyl group, at least one of $R^{20}$ and $R^{21}$ being a hydrogen group; and r is a polymerization degree. It should be noted that the liquid oligomer of conjugated diene is not restricted to a polymer having 1,2-linked conjugated diene units in a chain as shown in the formula (17), but may be a polymer having 1,4-linked conjugated diene units.

$R^{18}$ and $R^{19}$ are independently any one of the above (I)-(III), without restriction as long as at least one of $R^{18}$ and $R^{19}$ is the above (I). A specific example of $R^{18}$ and $R^{19}$ is a (meth)acrylic group. Another atom group, which may be contained in $R^{18}$ and $R^{19}$, is at least one selected from the group consisting of an urethane bond, an ester bond, an ether bond, an isocyanate group, a hydroxyl group, a carboxylic group and an alkoxyl group.

Though not particularly restricted, the number-average molecular weight of the liquid oligomer of conjugated diene is preferably 500-50,000. Commercially available liquid oligomers of conjugated dienes represented by the formula (17) are, for instance, NISSO-PB TEA-1000 and NISSO-PB TE-2000 available from Nippon Soda Co., Ltd., etc.

The liquid oligomer of conjugated diene may contain other conjugated dienes as polymerizable components, if necessary. When the liquid oligomer of conjugated diene is a butadiene oligomer or its derivatives, it may contain isoprene as a comonomer. When the liquid oligomer of conjugated diene is an isoprene oligomer or its derivatives, it may contain butadiene as a comonomer. Other conjugated dienes may be 2,3-dimethyl-1,3-butadiene, 1,3-pentadiene, 2-methyl-1,3-pentadiene, 1,3-hexadiene, 4,5-diethyl-1,3-octadiene, 3-butyl-1, 3-octadiene, chloroprene, etc. The liquid oligomer of conjugated diene may contain an olefin as a comonomer, which may be random-, block- or graft-copolymerized.

The liquid oligomer of conjugated diene may be hydrogenated. The hydrogenated liquid oligomer of conjugated diene is preferably represented by the following general formula (18):

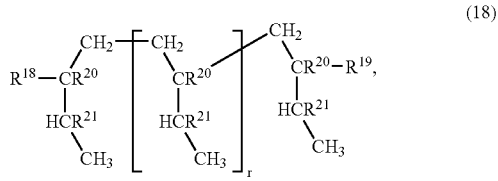

(18)

wherein $R^{18}$-$R^{21}$ and r are the same as in the formula (17). Commercially available hydrogenated liquid oligomers of conjugated dienes represented by the formula (18) are, for instance, NISSO-PB TEAI-1000 available from Nippon Soda Co., Ltd., etc.

(iv) Liquid Oligomers of Vinyl Aromatics and Conjugated Dienes

The liquid oligomers of vinyl aromatics and conjugated dienes are copolymers having at least a vinyl aromatic unit and a conjugated diene unit and at least one ethylenically unsaturated bond in a molecule. The vinyl aromatic component is preferably styrene. The conjugated diene components are preferably isoprene and 1,3-butadiene. A ratio of the vinyl aromatic component to the conjugated diene component in the liquid oligomers of vinyl aromatics and conjugated dienes is not particularly restricted, but may be determined depending on the demanded properties such as toughness, plasticity, mechanical strength, etc.

The liquid oligomers of vinyl aromatics and conjugated dienes may be modified by introducing functional groups or other atom groups, or by hydrogenation, etc. The functional groups may be a (meth)acrylic group, an isocyanate group, a hydroxyl group, a carboxylic group, an alkoxyl group, a sulfonic group, an epoxy group, a hydrocarbon group, etc. The other atom groups may be an urethane bond, an ester bond, an ether bond, etc. Commercially available liquid oligomers of vinyl aromatics and conjugated dienes are, for instance, Kuraprene LIR-310 available from Kuraray Chemical Co., Ltd., etc.

(v) Fluoro-group-containing, Unsaturated Monomers

By containing the fluoro-group-containing, unsaturated monomer as a comonomer, the phosphorus-acid-group-containing (meth)acrylamide polymer is provided with improved heat resistance and water resistance. The fluoro-group-containing, unsaturated monomers may be, for instance, hydrofluoroalkyl group-containing (meth)acrylate such as perfluorooctyl ethyl(meth)acrylate, etc.; perfluoroalkyl group-containing (meth)acrylate; hydrofluoroalkyl group-containing (meth)acrylic acid such as α-(trifluoromethyl) acrylic acid, etc.; perfluoroalkyl group-containing vinyl such as perfluorobutyl ethylene, perfluorohexyl ethylene, perfluorooctyl ethylene, perfluorodecyl ethylene, etc.; hydrofluoroalkyl group-containing vinyl, etc.

(vi) Compounds having pluralities of ethylenically unsaturated bonds in a molecule without acid group To improve the solvent resistance of the phosphorus-acid-group-containing (meth)acrylamide polymer, it is preferable to cross-link the phosphorus-acid-group-containing (meth)acrylamide polymer by using an unsaturated compound containing pluralities of ethylenically unsaturated bonds without acid group. Such cross-linking agents may be urethane acrylate obtained by reacting the above-described diisocyanate with glycerol di(meth)acrylate, ethylene glycol di(meth) acrylate, trimethylol propane tri(meth)acrylate, liquid oligomers of conjugated dienes and their derivatives, and liquid oligomers of vinyl aromatics and conjugated dienes and their derivatives. In addition, divinyl benzene, etc. may be used.

(c) Amount of Each Unsaturated Compound

The mass ratio (A)/(B) of the phosphorus-acid-group-containing (meth)acrylamide (A) to the other unsaturated compound (B) is not particularly restricted, but may be properly determined depending on the demanded properties. The mass ratio (A)/(B) is preferably in a range of 100/0-5/95. The lower limit of this ratio is more preferably 10/90 or more, further preferably 20/80 or more. In the other unsaturated compound (B), the mass ratio (a)/(b) of the above acid-group-containing, unsaturated compound (a) to the above unsaturated compound containing no acid group (b) is preferably 100/0-5/95, more preferably 95/5-20/80, though not particularly restricted. The amount of the cross-linking agent is preferably 0.5% or more by mass, more preferably 1% or more by mass, per 100% by mass of the total amount of the phosphorus-acid-group-containing (meth)acrylamide and the other unsaturated compound.

(2) Production method of Phosphorus-acid-group-containing (Meth)acrylamide Polymer The phosphorus-acid-group-containing (meth)acrylamide polymer can be produced by radiation- or thermal-polymerizing (i) the phosphorus-acid-group-containing (meth)acrylamide, or (ii) a mixture of the phosphorus-acid-group-containing (meth)acrylamide and the other unsaturated compound. Unless otherwise mentioned, the phosphorus-acid-group-containing (meth)acrylamide, and the mixture of the phosphorus-acid-group-containing (meth)acrylamide and the other unsaturated compound are both called "unsaturated starting materials."

(a) Production Method by Radiation Polymerization

The radiations are preferably light rays, X-ray, electron beams, etc., and the light rays are preferable. The light rays may be visible light rays, ultraviolet rays, etc., and the ultraviolet rays are preferable. The method of the present invention for producing the polymer will be explained below, taking the production of a phosphorus-acid-group-containing (meth)acrylamide polymer membrane by ultraviolet polymerization for example. The production method of a polymer membrane by ultraviolet polymerization comprises casting a composition (unsaturated composition) comprising an unsaturated starting material and a photopolymerization initiator (photosensitizer) on a plate coated with a material (fluoropolymer, etc.), to which the unsaturated composition is not adhered, covering the unsaturated composition with an ultraviolet-transmitting plate, and irradiating ultraviolet rays to the unsaturated composition for polymerization.

The photopolymerization initiators (photosensitizers) addable to the unsaturated starting material may be (i) Adjacent polyketone compounds represented by R—(CO)$_n$—R', wherein R and R' are a hydrogen group or a hydrocarbon group, and x is 2-3; for instance, diacetyl, dibenzyl, (ii) α-carbonyl alcohols represented by R—CO—CHOH—R', wherein R and R' are a hydrogen group or a hydrocarbon group; for instance, benzoin, (iii) Acyloin ethers represented by R—CH(OR")—CO—R', wherein R, R' and R" are a hydrocarbon group; for instance, benzoin methyl ether, (iv) α-Substituted acyloins represented by Ar—CR(OH)—CO—Ar, wherein Ar is an aryl group, and R is a hydrocarbon group; for instance, α-alkyl benzoin, and (v) Polynuclear quinones, for instance, 9,10-anthraquinone.

These photopolymerization initiators may be used alone or in combination.

The amount of the photopolymerization initiator used is preferably 0.005-10% by mass, more preferably 0.01-5% by mass, per the total amount of the unsaturated starting material. When it is less than 0.005% by mass, polymerization is not completed within the predetermined ultraviolet irradiation time, undesirably leaving the unreacted monomer. When it is more than 10% by mass, the resultant polymer is too low in polymerization degree and undesirably colored.

The ultraviolet-transmitting plate and the supporting substrate used for the ultraviolet polymerization of the unsaturated composition should have high ultraviolet transmittance, sufficient heat resistance to withstand high temperatures at the time of ultraviolet polymerization, no adhesion to the unsaturated composition and its polymer, and good releasability.

A flat glass plate usually used as the supporting substrate has extremely high ultraviolet transmittance and heat resistance, but it adheres to the polymer. It is thus preferable to coat a silicone- or fluoro-release agent or attach a thin transparent fluororesin film to the flat glass plate in advance.

Usable as the supporting substrate, in addition to the flat glass plate, is a flat resin plate having high ultraviolet transmittance and heat resistance of 100° C. or higher, which is made of fluororesins such as polyperfluorovinyl ether resins (PFA) and polyvinylidene fluoride resins (PVDF); poly3-methylpentene resins; polypropylene resins; etc.

To impart releasability to the polymer, a release agent may be added to the unsaturated composition in advance. The release agent preferably has good compatibility with the unsaturated composition. The release agents are preferably fluoro-surfactants, and fluoroalcohols are particularly preferable among them. Specific examples of the release agents are perfluorooctyl ethanol, perfluorooctyl sulfoamide ethanol and their ethylene oxide adducts; hydrocarbon surfactants; high-molecular-weight polyoxyethylene glycol (for instance, Carbowax), etc. The amount of the release agent added is 0.5-5% by mass, preferably 0.5-1.5% by mass, per the total amount of the unsaturated composition. When it is less than 0.5% by mass, the releasability is insufficient. When it is more than 5% by mass, the releasing effect is saturated.

Figure 2:
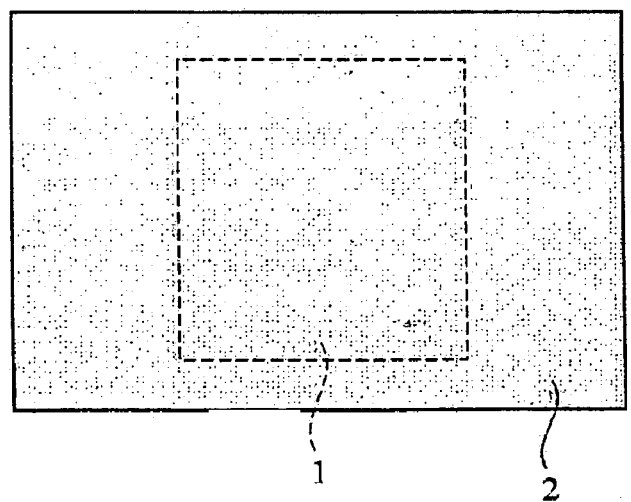
FIG. 2 is a plan view showing an unsaturated composition sandwiched by two flat glass plates.

With the unsaturated composition cast and covered with the ultraviolet-transmitting plate, air and excess unsaturated composition should be squeezed out before the ultraviolet irradiation. For instance, as shown in FIGS. 1 and 2, the composition 1 is preferably sandwiched by two supporting substrates 2, 2, clamped with uniform pressure by clips 3, and subjected to ultraviolet irradiation in a horizontal state. The irradiation is conducted for 1-15 minutes on at least one surface. When the irradiation is conducted on both surfaces alternately, it is 0.5-15 minutes for each surface. The ultraviolet irradiation intensity for polymerization is 5-150 mW/cm$^2$, preferably 10-120 mW/cm$^2$. The distance of ultraviolet irradiation is properly determined to achieve full curing in the above irradiation time range. A membrane obtained by ultraviolet polymerization may be heat-treated at 100-130° C. for about 1-15 minutes to improve mechanical strength and solvent resistance. The ultraviolet-polymerized membrane is as thick as usually 20-500 μm, preferably about 20-200 μm.

In the present invention, to assist the dissolving of the photopolymerization initiator in the unsaturated starting material, a low-boiling-point solvent such as methanol, the above N,N-dialkyl(meth)acrylamide may be added as a diluent. Particularly N,N-dialkyl(meth)acrylamide is preferable because it is polymerized with the unsaturated starting material by ultraviolet polymerization. As the N,N-dialkyl(meth)acrylamide, N,N-dimethyl acrylamide (DMAA) and N,N-dimethylmethacrylamide are preferably used. In the case of N,N-dialkyl(meth)acrylamide, it is used as a solvent in the preparation of phosphorus-acid-group-containing (meth)acrylamide, and the resultant reaction solution is polymerized. The polymer is thus produced efficiently. Although the production method of a polymer membrane by ultraviolet polymerization has been explained above, essentially the same procedures can be adopted in the case of using other radiations such as X-ray, electron beams, etc. When X-ray or electron beams are used, the photopolymerization initiator may not be used.

(b) Production Method by Thermal Polymerization

The method for producing a phosphorus-acid-group-containing (meth)acrylamide polymer by thermal polymerization will be explained. A radical polymerization reaction is conducted in a common solvent, in which both the unsaturated starting material and the formed polymer are dissolved, using an organic peroxide initiator such as ammonium persulphate (APS), potassium persulphate (KPS), acetyl peroxide, isopropyl hydroperoxide, etc.; an azo initiator such as 2,2'-azobisisobutylonitril, 2,2'-azobis(2,4-dimethyl valeronitrile), dimethyl 2,2'-azobis(2-methyl propyonate), dimethyl-2,2'-azobisisobutyrate, etc.; or a peroxide initiator such as lauryl peroxide, benzoyl peroxide, tert-butyl peroxypivalate, hydrogen peroxide, etc. as a polymerization initiator.

The solvent is preferably an alcohol and/or a polar solvent. The alcohol is preferably an aliphatic lower alcohol, and the aliphatic lower alcohol is preferably at least one selected from the group consisting of methanol, ethanol and isopropyl alcohol. They may be used in combination. Esters, dioxane, ethers, etc. may be added in a range not deteriorating the solubility. The polar solvent is more preferably at least one selected from the group consisting of dimethylformamide (DMF), dimethyl sulfoxide (DMSO) and water. When water is used, the aliphatic lower alcohol is preferably used together.

The phosphorus-acid-group-containing (meth)acrylamide polymer produce by using the above cross-linking agent is not dissolved in an alcohol or a polar solvent, resulting in difficulty in film-forming. Accordingly, it is preferable to produce a membrane of the cross-linked, phosphorus-acid-group-containing (meth)acrylamide polymer by the above radiation polymerization.

Polymerization procedures will be explained below. A solution of an unsaturated starting material in a solvent is charged into a reactor equipped with a stirrer and a reflux condenser, and the reactor is filled with a nitrogen atmosphere, and then heated to 40-70° C., which is the decomposition temperature of a polymerization initiator added. The preferred polymerization temperature is 50-70° C. Immediately after reaching the predetermined temperature, the polymerization initiator is added. At this time, slight heat generation occurs, confirming the initiation of the polymerization. After reaching the predetermined temperature, the polymerization initiator is added 2-3 times at an interval of about 1 hour, to continue a polymerization reaction for about 1 hour. The reaction temperature need not be constant from the beginning to the end, but may be elevated at the end of the polymerization to reduce an unreacted monomer as much as possible.

The initial solid concentration of the unsaturated starting material in the polymerization solution is preferably 10-40% by mass, more preferably 10-30% by mass. The total amount (mass ratio) of the polymerization initiator used is preferably 0.1-5, more preferably 0.1-2, per 100 of the unsaturated starting material.

To isolate the phosphorus-acid-group-containing (meth) acrylamide polymer, the polymerization solution is concentrated until its solid content becomes 10-80% by mass, and the concentrated solution is added to a poor solvent to precipitate a viscous solid, which is filtered out. Because the reacted solution may contain not only the desired phosphorus-acid-group-containing (meth)acrylamide polymer, but also impurities such as isolated phosphoric acid, the unreacted monomer, low-polymerization-degree components, etc., it is preferably purified, though not restrictive. The purification is conducted by concentrating the polymerization solution until its solid content becomes 10-80% by mass, introducing the concentrated solution into a poor solvent to precipitate a viscous solid, and removing the poor solvent by decantation. The poor solvent is preferably acetone, THF, ether, 1,1,1-trichloroethane, etc. The poor solvent is used in such an excess amount as 2-15 times by volume the reaction product. The washing operation of the viscous solid with the poor solvent may be repeated, if necessary. Such purification can remove the above impurities.

To form the phosphorus-acid-group-containing (meth) acrylamide polymer prepared by thermal polymerization into a membrane, it is preferable to use a casting method, which comprises casting a solution of a phosphorus-acid-group-containing (meth)acrylamide polymer on a horizontal glass plate or tray, and evaporating a solvent. The resultant film (membrane) is preferably heat-treated at 100-140° C. for about 1-30 minutes under normal or reduced pressure to improve its mechanical strength and solvent resistance. The cast membrane may be stretched to increase mechanical strength. The stretching is preferably conducted while heating. The cast membrane is as thick as usually 20-500 μm, preferably about 20-200 μm.

(3) Properties of Phosphorus-acid-group-containing (Meth)acrylamide Polymer

The phosphorus-acid-group-containing (meth)acrylamide polymer obtained by each of the above production methods has a relatively low molecular weight. Though not particularly restricted, the phosphorus-acid-group-containing (meth)acrylamide polymer preferably has such a polymerization degree as to have a viscosity of about 3-200 mPa·s (cP) when turned to a methanol solution with a solid concentration of 10-25% by mass. The phosphorus-acid-group-containing (meth)acrylamide polymer usually exhibits surface intrinsic resistivity of $1 \times 10^7$ Ω·cm or less under the conditions of room temperature and RH of 50-75%, presumably because the polymer has a high phosphonic group. Particularly a polymer made only of the phosphorus-acid-group-containing (meth) acrylamide is mainly composed of hydrocarbon skeletons formed by ethylenically unsaturated bonds, amide groups and phosphorus acid groups, without ester groups, so that it is harder than polymers containing many ester groups.

[5] Conductive Resins

The conductive resin of the present invention comprises the above phosphorus-acid-group-containing (meth)acrylamide polymer as an indispensable component. The conductive resin may contain other resins, with which the phosphorus-acid-group-containing (meth)acrylamide polymer has excellent compatibility. Accordingly, the conductive resin comprising other resins exhibits excellent conductivity owned by the phosphorus-acid-group-containing (meth)acrylamide polymer, and excellent film-forming properties, chemical resistance, plasticity, transparency, high adhesion to various substrates, etc. owned by the other resins.

(1) Other Addable Resins

The other resin is preferably at least one selected from the group consisting of unsaturated alcohol copolymers comprising unsaturated alcohol units and vinyl halide units and/or aliphatic acid vinyl ester units (unless otherwise mentioned, simply called "unsaturated alcohol copolymers"), partially acetalized unsaturated alcohol polymers, melamine resins (for instance, trimethoxymethyl melamine resin, etc.), poly (meth)acrylonitrile, poly(meth)acrylate, polyacrylamide, poly(meth)acrylic acid, polyacetal, urethane resins, cellulose and its modified products, polystyrene, polyvinyl chloride, and polyvinyl acetate. Preferable among them are the unsaturated alcohol copolymers, the acetalized unsaturated alcohol polymers, and the melamine resins.

(a) Unsaturated Alcohol Copolymers

The unsaturated alcohol copolymers comprise at least unsaturated alcohol units and vinyl halide units and/or aliphatic acid vinyl ester units. The unsaturated alcohol units may be vinyl alcohol units, allyl alcohol units, etc., and the vinyl alcohol units are preferable from the aspect of cost. Vinyl alcohol exists not as a monomer, but as a vinyl(co) polymer-constituting unit. To obtain the vinyl alcohol unit, a hydroxyl-group-containing vinyl (co)polymer containing vinyl acetate units need only be prepared and saponified.

The unsaturated alcohol copolymer having vinyl alcohol units may be represented by the following general formula (19):

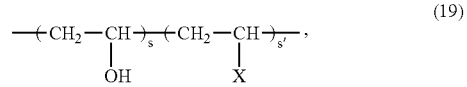

(19)

wherein X is a halogen atom or an —OCOR group, which may be different in the repeating units, R is an alkyl group, and s and s' are respectively a polymerization degree.

The aliphatic acid vinyl ester units may be a vinyl acetate unit, a vinyl propionate unit, a vinyl butyrate unit, etc., and the vinyl acetate unit is preferable. The vinyl halide units may be a vinyl chloride unit, a vinyl fluoride unit, a vinyl bromide unit, etc., and the vinyl chloride unit is preferable. The numbers of the unsaturated alcohol units, the aliphatic acid vinyl ester units and the vinyl halide units contained may be two or more.

When the unsaturated alcohol copolymer contains vinyl halide units, the percentage of the vinyl halide units is pref erably 20-95 mol %, per the total amount (100 mol %) of vinyl monomer units constituting the unsaturated alcohol copolymer. When it is less than 20 mol %, the copolymer has low water resistance and solvent resistance. The percentage of the unsaturated alcohol units in the unsaturated alcohol copolymer containing vinyl halide units is preferably 5-80 mol %, per the total amount (100 mol %) of vinyl monomer units constituting the unsaturated alcohol copolymer. Though not particularly restricted, the percentage of the aliphatic acid vinyl ester units in the unsaturated alcohol copolymer containing vinyl halide units may be 30 mol % or less, per the total amount (100 mol %) of vinyl monomer units constituting the unsaturated alcohol copolymer.

When the unsaturated alcohol copolymer is composed only of the unsaturated alcohol units and the aliphatic acid vinyl ester units, the percentage of the aliphatic acid vinyl ester units is preferably 40-95 mol %, more preferably 50-80 mol %, per the total amount (100 mol %) of vinyl monomer units constituting the unsaturated alcohol copolymer, though not restrictive. The unsaturated alcohol copolymer containing 40 mol % or more of aliphatic acid vinyl ester units has excellent water resistance and solvent resistance due to alkyl groups in the aliphatic acid vinyl ester units. However, the percentage of the aliphatic acid vinyl ester units is not restricted to 40-95 mol %, and copolymers containing less than 40 mol % of aliphatic acid vinyl ester units (for instance, polyvinyl alcohol having a saponification degree of more than 60) may be used, if necessary. In the case of using the unsaturated alcohol copolymer composed only of unsaturated alcohol units and aliphatic acid vinyl ester units, it is preferable to add melamine resins to improve the water resistance of the conductive resin.

The unsaturated alcohol copolymer may be prepared by copolymerizing at least unsaturated alcohol, vinyl halide and/or aliphatic acid vinyl by a known method. The unsaturated alcohol copolymer containing aliphatic acid vinyl ester units (for instance, vinyl alcohol units) is preferable produced by preparing a polymer from aliphatic acid vinyl (for instance, vinyl acetate) or its monomer composition, and partially saponifying the polymer. Though not particularly restricted, the average polymerization degree of the unsaturated alcohol copolymer is preferably 100-3,000.

Commercially available unsaturated alcohol copolymers may be used, and polyvinyl alcohol having vinyl acetate units may be, for instance, Kuraray LM Polymer (Poval) and EXCEVAL (registered trademarks, available from Kuraray Chemical Co., Ltd.), and GOHSENOL (registered trademark, available from The Nippon Synthetic Chemical Industry Co., Ltd.). The saponification degree of the polyvinyl alcohol having vinyl acetate units may be determined as described above. The unsaturated alcohol copolymer having vinyl acetate units, vinyl chloride units and vinyl alcohol units may be, for instance, SOLBIN A, SOLBIN AL, SOLBIN TA5R, SOLBIN TAO (registered trademarks, available from Nissin Chemical Industry Co., Ltd.), etc.

(b) Partially Acetalized Unsaturated Alcohol Polymer

The partially acetalized unsaturated alcohol polymer is obtained by reacting an unsaturated alcohol polymer having unsaturated alcohol units as a main component with aldehyde at a predetermined ratio, and partially acetalizing the product. The unsaturated alcohol polymer to be partially acetalized is preferably polyvinyl alcohol.

The unsaturated alcohol polymer obtained by partially acetalizing polyvinyl alcohol is represented by the following general formula (20):

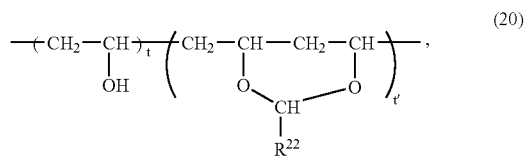

wherein $R^{22}$ is an alkyl group, and $t$ and $t'$ are respectively a polymerization degree. The partially acetalized unsaturated alcohol polymer may contain vinyl halide units and/or aliphatic acid vinyl ester units. The contents of the vinyl halide units and aliphatic acid vinyl ester units may be the same as described above.

The partially acetalized unsaturated alcohol polymer has excellent toughness, plasticity, adhesion, etc. because of acetal groups. Further, it has excellent water resistance and solvent resistance because of alkyl groups in the acetal groups. In addition, because the partially acetalized unsaturated alcohol polymer is cross-linkable by the acetal groups, it is provided with further improved water resistance by heating, etc. Though not particularly restricted, the aldehyde used for acetalization is preferably butyl aldehyde. Thus, the partially acetalized unsaturated alcohol polymer is preferably partially butyralized polyvinyl alcohol.

The acetalization degree of the partially acetalized unsaturated alcohol polymer is preferably 0-80 mol %, 20-90 mol % of hydroxyl groups remaining per 100 mol % of the hydroxyl groups before acetalization. Though not particularly restricted, the average polymerization degree of the partially acetalized unsaturated alcohol polymer is preferably 100-3,000. The partially acetalized unsaturated alcohol polymer is commercially available, for instance, S-LEC B and S-LEC K (available from Sekisui Chemical Co., Ltd.).

The above unsaturated alcohol copolymer (a) and the above partially acetalized unsaturated alcohol polymer (b) may contain other unsaturated monomer units, which are (meth)acrylonitrile, (meth)acrylate, (meth)acrylamide, alkyl-amino-group-containing, unsaturated monomers, substituted or unsubstituted styrenes, vinyl monomers, olefins (for instance, ethylene, etc.), dienes, etc.

The unsaturated alcohol copolymer and the partially acetalized unsaturated alcohol polymer may be phosphatized, if necessary. A method for turning them to phosphates may be the same as the above method for adding (poly)phosphonic acid to the (meth)acrylamide monomer, except for using 0.5-0.55 mole equivalent of phosphoric anhydride to the hydroxyl group. However, hydrolysis need not be conducted after all $P_2O_5$ is added, but water may be added together with $P_2O_5$.

The phosphatized, unsaturated alcohol copolymer and the phosphatized, partially acetalized unsaturated alcohol polymer may be formed into complexes to improve conductivity and heat resistance. The complexes are preferably ammonium salts, amine salts or metal salts, as in the phosphorus-acid-group-containing (meth)acrylamide.

(2) Formulation of Other Resins

The ratio of the phosphorus-acid-group-containing (meth)acrylamide polymer to the other resin is preferably 0.05 or more, more preferably 0.1 or more, by mass on a solid basis. When this ratio is less than 0.05, the conductivity is insufficient. The upper limit of this ratio is not particularly restricted, but may be determined depending on desired properties.

(3) Method of Adding Other Resins (a) Mixing Polymerization Method

The conductive resin containing other resins is obtained by subjecting the above unsaturated starting material [phosphorus-acid-group-containing (meth)acrylamide (+the above other unsaturated compound)] to radiation or thermal polymerization in the presence of the other resins. Particularly to produce the conductive resin comprising the cross-linked, phosphorus-acid-group-containing (meth)acrylamide polymer, radiation polymerization is used. Because the radiation or thermal polymerization method may be the same as in the case of the above phosphorus-acid-group-containing (meth) acrylamide polymer, its explanation will be omitted.

(b) Solution-mixing Method

The conductive resin containing other resins may also be obtained by adding other resins to the phosphorus-acid-group-containing (meth)acrylamide polymer solution, and heat-treating the resultant polymer solution. The polymer solution preferably has a resin concentration of 5-30% by mass. A solvent is evaporated from the polymer solution by heating, and a solid conductive resin having a uniform composition can be obtained by heating at 100-140° C. The conductive resin thus obtained has plasticity and transparency.

Particularly when the melamine resin is added, the (poly) phosphonic group in the polymer acts as a catalyst by heating the solvent-removed resin composition at 100-140° C., accelerating the cross-linking reaction of the melamine resin, and thus improving the mechanical strength and solvent resistance of the conductive resin. With methylol melamine or methylated or butylated methylol melamine added as the melamine resin, the phosphorus-acid-group-containing (meth)acrylamide polymer may be heat-treated for polymerization.

(4) Properties of Conductive Resins

The above conductive resin usually has surface intrinsic resistivity of $10^4$-$10^7$ Ω·cm under the conditions of a relative humidity of 50-75% and room temperature, particularly $10^4$-$10^5$ Ω·cm under the conditions of a relative humidity of 75% and room temperature. The conductive resin also has excellent water resistance, chemical resistance and adhesion to various substrates. The conductive resin having such properties may be usefully interposed between a bioelectrode and a skin. Because the conductive resin contains phosphorus atoms, it is excellent in flame retardance and inorganic filler dispersibility. The conductive resin can be formed into cast membranes by the above-described method.

[6] Coating Agent

The coating agent of the present invention comprises the above conductive resin. Usable solvents are those for thermal polymerization described in [4] above. When the coating agent is used, it is preferably diluted by a good solvent to a suitable concentration. The good solvents are preferably aliphatic lower alcohols described in [4] above. Because the cross-linked, phosphorus-acid-group-containing (meth)acrylamide polymer is insoluble in a solvent, an uncross-linked, phosphorus-acid-group-containing (meth)acrylamide polymer is used for the coating agent.

The coating agent may properly contain usual additives such as viscosity modifiers (for instance, thickeners), various coloring pigments for decoration, opacifying fillers, leveling agents for improving coating flatness, coupling agents for improving adhesion to substrates, as well as known antioxidants, lubricants, antiblocking agents, antiaging agents, flame retardants, conductive agents, defoaming agents, etc.

The coating agent is applied to an object to a dry thickness of 1-100 μm, and heated to form a coating with antistaticity, conductivity, antifogging property, etc. The coating of a substrate surface may be conducted by brush-coating, bar coating, spraying, immersion, roll-coating, blade-coating, flow-coating or electrostatic coating. The coating agent can be applied to any of metal plates, glass plates, plastic moldings, sheets or films, fibers, woven or nonwoven fabrics, etc. with good adhesion. A film obtained by curing the coating agent has excellent adhesion to the substrate, solvent resistance, water resistance, hardness, gloss, weathering resistance, rust resistance, etc.

[7] Polymer Electrolyte Membrane

The polymer electrolyte membrane of the present invention utilizes the above conductive resin as a solid polymer electrolyte. This membrane has excellent proton conductivity derived from high-density (poly)phosphonic groups.

The polymer electrolyte membrane is obtained by (a) radiation-polymerizing the phosphorus-acid-group-containing (meth)acrylamide, or a its composition containing the above other unsaturated compound and/or resin, if necessary, which is sandwiched by ultraviolet-transmitting supporting substrates, or (b) thermally polymerizing and then casting it. Because radiation polymerization, thermal polymerization and casting may be the same as described above, their explanation will be omitted.

The polymer electrolyte membrane preferably comprises a cross-linked, phosphorus-acid-group-containing (meth)acrylamide polymer. The cross-linked polymer electrolyte membrane has excellent solvent resistance, particularly methanol resistance. To produce the polymer electrolyte membrane comprising a cross-linked, phosphorus-acid-group-containing (meth)acrylamide polymer, the radiation polymerization method is preferably used as described above.

In the radiation polymerization method, a reinforcing substrate is impregnated or coated with the unsaturated composition, and the unsaturated composition is photopolymerized by ultraviolet irradiation to form a composite membrane, with the reinforcing substrate sandwiched by ultraviolet-transmitting supporting substrates. Usable reinforcing substrates are, for instance, reinforcing inorganic fibers described in WO 2002/33709, reinforcing organic fibers, and resin films. To reduce the viscosity of the unsaturated composition, to facilitate the impregnation of a reinforcing substrate with the unsaturated composition, and to reduce the amount of the unsaturated composition attached to the reinforcing substrate to make the composite membrane thinner, etc., low-boiling-point solvents such as methanol, and the above N,N-dialkyl (meth)acrylamide may be added as diluents.

The ratio of the reinforcing substrate to the unsaturated composition may largely differ depending on the affinity of the unsaturated composition for the reinforcing substrate, in other words, the absorbability of the unsaturated composition, but the mass ratio of (reinforcing substrate)/(unsaturated composition) is generally 1/20-1/2.

The above polymer electrolyte membrane is suitable for electrolyte membranes for primary batteries, secondary batteries and fuel cells, display elements, various sensors, signal-transmitting media, solid capacitors, ion exchange membranes, etc. Because the polymer electrolyte membrane of the present invention has excellent proton conductivity of $10^{-4}$-$10^{-2}$ S·cm$^{-1}$ with small temperature dependency, it is suitable for electrolyte membranes for fuel cells.

[8] Fuel Cell

The fuel cell may have a known structure. The fuel cell is usually constructed by alternately laminating pluralities of unit fuel cells (membrane-electrode assemblies) via separators. The unit fuel cell is constituted by a polymer electrolyte membrane, and electrodes (anode and cathode) on both sides. Each electrode comprises a gas diffusion layer (porous carbon sheet, etc.) and a catalyst layer (platinum particles, etc.). The catalyst layer is formed by coating catalyst particles on the gas diffusion layer.

The separator separates a fuel gas (hydrogen, methane, methanol, etc.) from an oxidizing gas (oxygen or air), provides paths for the fuel gas and the oxidizing gas, and leads electricity generated by the fuel cell outside. Accordingly, the separator is made of conductive materials such as carbon materials, carbon composite materials (for instance, carbon and thermosetting or thermoplastic resins), metal materials, metal composite materials (for instance, metal and carbon), etc. The separator is provided with grooves (reaction gas paths) acting as paths for the fuel gas and the oxidizing gas, on a surface in contact with the electrode.

The present invention will be explained in further detail by Examples below without intention of restricting the present invention thereto.

EXAMPLE 1

122.3 g (1.72 mole) of acrylamide, and 1.0 g of hydroquinone monomethyl ether were charged into an automatic synthesis reactor having an inner volume of 500 mL available from UNI-CHEMICAL CO. LTD., to which a reflux condenser, a powder inlet and a thermometer were connected, dissolved in 120.6 g of DMF, and heated to 60° C. After confirming that the inside-reactor temperature reached 60° C., 134.0 g (0.94 mole) of phosphoric anhydride was added with five installments over 3 hours 30 minutes. During adding phosphoric anhydride, the inside-reactor temperature was kept within 60-95° C. while stirring at 300-400 rpm. After all phosphoric anhydride was added, an aging reaction was conducted at 80° C. for 2 hours.

A reaction solution containing the resultant intermediate product had a solid concentration of 63% by mass, when measured by taking 0.5 g of the reaction solution, diluting it with 5 g of methanol, and drying it with hot air at 100° C. for 1 hour. The same concentration-measuring method was also used below. The acid value of the intermediate product was measured by dissolving 1 g of the reaction solution in 100 g of DMSO, and measuring the acid value with a 1-N aqueous KOH solution with titration termination at pH of 10.3. The same acid-value-measuring method was also used below. The results are shown in Table 3. It is presumed that the intermediate product (acid value: 444 mg/g) is mainly composed of pyrophosphonic diacrylamide (theoretical acid value: 394 mg/g), and a compound (theoretical acid value: 526 mg/g) having pyrophosphoric acid N,N-linked to acrylamide or a compound (theoretical acid value: 526 mg/g) having two acrylamide molecules bond via dipyrophosphoric acid (see the above formula (8). When part of the reaction solution was mixed with water, it became cloudy, presumably because water-insoluble acrylonitrile was by-produced.

Because a trace amount of a solid was precipitated in the cooled reaction solution, it was separated by suction filtration. 330 g of the resultant transparent liquid was mixed with 14.76 g (0.82 mole) of water, and heated at a temperature of 70-80° C. for 30 minutes while stirring to cause hydrolysis. The acid value of the product was measured on 1 g of the hydrolyzed reaction solution (solid concentration: 64% by mass). The results are shown in Table 3. It is presumed that the product (acid value: 795.3 mg/g) is mainly composed of phosphonic acrylamide (theoretical acid value: 741.7 mg/g), and further contains N,N-diphosphonic acrylamide (theoretical acid value: 969.7 mg/g), or a polyphosphonic-group-containing monomer represented by the above formula (7).

The liquid chromatography analysis of the resultant composition revealed that the total amount of phosphonic acrylamide, N,N-diphosphonic acid acrylamide, and the polyphosphonic-group-containing monomer represented by the above formula (7) was 70% or more by mass, and that the composition further contained 5% or less by mass of by-produced acrylonitrile. The analysis conditions by liquid chromatography using SPD-10A comprising a UV detector available from Shimadzu Corp. were as follows:

Column temperature: room temperature,
Solvent: methanol/water (7/3 by mass),
Concentration: 0.01% by mass (injected amount: 2.5 µl),
Column: PRP-1 of HAMILTON, and
Flow rate of solvent: 0.3 ml/minute.

EXAMPLE 2

142 g (2.0 mole) of acrylamide, and 1.0 g of hydroquinone monomethyl ether were charged into the same automatic synthesis reactor as in Example 1, dissolved in 198 g (2.0 mole) of N,N-dimethyl acrylamide (DMAA), and heated to 70° C. After confirming that the inside-reactor temperature reached 70° C., 156 g (1.1 mole) of phosphoric anhydride was introduced with five installments over 3 hours through a powder inlet. During adding phosphoric anhydride, the inside-reactor temperature was kept within 70-95° C. while stirring at 300-400 rpm. After all phosphoric anhydride was added, an aging reaction was conducted at 80° C. for 2 hours.

The resultant solution was mixed with 19.8 g (1.1 mole) of water, and heated at a temperature of 70-95° C. for 30 minutes while stirring to cause hydrolysis. The refractive index of the resultant reaction solution was measured at a temperature of 20° C., using a hand-held Refractometer 500 available from Atago Co., Ltd. The same refractive-index-measuring method was also used below. The acid value of the product was measured on 1 g of the reaction solution (solid concentration: 61.5% by mass). Each result is shown in Table 3. It is presumed that the product (acid value: 760 mg/g) was phosphonic acrylamide (theoretical acid value: 741.7 mg/g).

EXAMPLE 3

As shown in Table 3, a reaction solution (solid concentration: 53% by mass) containing an intermediate product was prepared in the same manner as in Example 1, except for using 71 g (1 mole) of acrylamide and 156 g (1.1 mole) of phosphoric anhydride as starting materials and 198 g of DMAc as a solvent. The acid value of the intermediate product was measured on 1 g of the reaction solution. It is presumed that the intermediate product (acid value: 550 mg/g) is either a compound (theoretical acid value: 525.8 mg/g) having pyrophosphoric acid N,N-linked to acrylamide or a compound (theoretical acid value: 525.8 mg/g) having two acrylamide molecules bonded via dipyrophosphoric acid [see the above formula (8)]. When part of the reaction solution was mixed with water, it became cloudy, presumably because water-insoluble acrylonitrile was by-produced.

The reaction solution containing an intermediate product was mixed with 20 g (1.1 mole) of water, and heated at 70-80° C. for 30 minutes while stirring to cause hydrolysis. The acid value of the product was measured on 1 g of the resultant hydrolyzed reaction solution (solid concentration: 55% by mass). The results are shown in Table 3. It is presumed that the product (acid value: 959.1 mg/g) was mainly N,N-diphosphonic acrylamide (theoretical acid value: 969.7 mg/g).

The liquid chromatography analysis of the resultant composition in the same manner as in Example 1 revealed that the total amount of phosphonic acrylamide, N,N-diphosphonic acid acrylamide, and a polyphosphonic-group-containing monomer represented by the above formula (7) was 90% or more by mass, and that the composition further contained 5% or less by mass of by-produced acrylonitrile.

EXAMPLE 4

As shown in Table 3, a reaction solution containing an intermediate product was prepared in the same manner as in Example 2, except for using 71 g (1 mole) of acrylamide, and adding phosphoric anhydride with eight installments. The resultant solution was hydrolyzed in the same manner as in Example 2. The refractive index of the resultant reaction solution was measured. The acid value of the product was measured on 1 g of the reaction solution (solid concentration: 55% by mass). Each result is shown in Table 3. It is presumed that the product (acid value: 975.6 mg/g) was N,N-diphosphonic acrylamide (theoretical acid value: 969.7 mg/g).

EXAMPLE 5

As shown in Table 3, A reaction solution containing an intermediate product was prepared in the same manner as in Example 2, except for using 207 g (1 mole) of t-butyl acrylamide sulfonic acid (TBAS available from Mitsubishi Rayon Co., Ltd.) and 78 g (0.55 mole) of phosphoric anhydride as starting materials, adding phosphoric anhydride with two installments over 2 hours, and conducting an aging reaction at a temperature of 70-95° C. for 1 hour. The acid value of the intermediate product was measured on 1 g of the resultant solution. The results are shown in Table 3. It is presumed that the resultant intermediate product (acid value: 404.0 mg/g) was di(t-butyl acrylamide sulfonic acid) pyrophosphonic acid (theoretical acid value: 402.9 mg/g).

When 9.9 g (0.55 mole) of water was added to 486 g of a solution containing the intermediate product at 70° C., its temperature was elevated to 90° C. Thereafter, it was heated at 70-90° C. for 30 minutes while stirring to cause hydrolysis. The refractive index of the resultant hydrolyzed reaction solution was measured. Also, the acid value of the product was measured on 1 g of the reaction solution (solid concentration: 58% by mass). Each result is shown in Table 3. It is presumed that the resultant product (acid value: 594.6 mg/g) was phosphonic-group-containing t-butyl acrylamide sulfonic acid (theoretical acid value: 585.4 mg/g).

EXAMPLE 6

55.42 g (0.7-8 mole) of acrylamide and 0.5 g of hydroquinone monomethyl ether were charged into the same automatic synthesis reactor as in Example 1, and dissolved in 100 g of the reaction solution [a solution of phosphonic-group-containing t-butyl acrylamide sulfonic acid in DMAA (concentration: 58% by mass)] prepared in Example 5. Using the resultant solution, as shown in Table 3, a reaction solution containing an intermediate product was prepared in the same manner as in Example 2 except for adding 62.24 g (0.44 mole) of phosphoric anhydride.

The resultant solution was mixed with 10 g (0.56 mole) of water, and kept at 70-95° C. for 30 minutes while stirring for hydrolysis. The refractive index of the resultant hydrolyzed reaction solution was measured. Also, the acid value of the product was measured on 1 g of the reaction solution (solid concentration: 80.7% by mass). Each result is shown in Table 3. The resultant reaction solution theoretically contains 0.68 mole (103.56 g) of phosphonic acrylamide (theoretical acid value: 741.7 mg/g) 0.10 mole (22.188 g) of N,N-diphosphonic acrylamide (theoretical acid value: 969.7 mg/g), and 0.20 mole (58 g) of phosphonic-group-containing t-butyl acrylamide sulfonic acid (theoretical acid value: 585.4 mg/g). This composition had an average theoretical acid value of 719.5 mg/g. Because the acid value of the product was 700 mg/g, it is presumed that the theoretically expected composition was substantially formed.

EXAMPLE 7

56.8 g (0.8 mole) of acrylamide, 0.5 g of hydroquinone monomethyl ether, 12 g (0.12 mole) of N,N-dimethyl acrylamide (DMAA), and 118 g of the reaction solution [a solution of phosphonic-group-containing t-butyl acrylamide sulfonic acid in DMAA (concentration: 58% by mass)] prepared in Example 5 were charged into the same automatic synthesis reactor as in Example 1, and heated to 70° C. After confirming that the inside-reactor temperature reached 70° C., 85.2 g (0.6 mole) of phosphoric anhydride was introduced with eight installments over 3 hours through a powder inlet. After the fifth addition of phosphoric anhydride, 0.3 g of hydroquinone monomethyl ether was added. During adding phosphoric anhydride, the inside-reactor temperature was kept within 70-95° C. while stirring at 300-400 rpm. After all phosphoric anhydride was added, an aging reaction was conducted at 80° C. for 2 hours.

The resultant solution was mixed with 18 g (1 mole) of water, and kept at 70-95° C. for 30 minutes while stirring for hydrolysis. The refractive index of the resultant hydrolyzed reaction solution was measured. Also, the acid value of the product was measured on 1 g of the reaction solution (solid concentration: 76.2% by mass). Each result is shown in Table 3. The resultant reaction solution theoretically comprises 0.4 mole (60 g) of phosphonic acrylamide (theoretical acid value: 741.7 mg/g), 0.4 mole (92 g) of N,N-diphosphonic acrylamide (theoretical acid value: 969.7 mg/g), and 0.24 mole (68.44 g) of phosphonic-group-containing t-butyl acrylamide sulfonic acid (theoretical acid value: 585.4 mg/g). This composition had an average theoretical acid value of 788.2 mg/g. Because the acid value of the product was 802 mg/g, it is presumed that the theoretically expected composition was substantially formed.

TABLE 3

| | | No. | | |
| --- | --- | --- | --- | --- |
| | | Example 1 | Example 2 | Example 3 |
| Reaction Mixture | (Meth)Acrylamide Monomer | Acrylamide 122.3 g (1.72 mole) | Acrylamide 142 g (2.0 mole) | Acrylamide 71 g (1 mole) |
| | Phosphoric Anhydride | 134 g (0.94 mole) | 156 g (1.1 mole) | 156 g (1.1 mole) |

TABLE 3-continued

|  |  | | | |
|---|---|---|---|---|
|  | Polymerization Inhibitor[1] | 1.0 g | 1.0 g | 1.0 g |
|  | Solvent | DMF[3] | DMAA[6] | DMAc[7] |
|  |  | 120.6 g | 198 g | 198 g |
|  |  |  | (2.0 mole) |  |
| Addition of | Adding Time (hrs.) | 3.5 | 3 | 3.5 |
| Phosphoric Anhydride | Number of installments | 5 | 5 | 5 |
| Reaction Conditions | Temperature (° C.) | 60-95 | 70-95 | 60-95 |
|  | Stirring (rpm) | 300-400 | 300-400 | 300-400 |
| Aging Conditions |  | 80° C. × 2 hrs. | 80° C. × 2 hrs. | 80° C. × 2 hrs. |
| Intermediate | Solid Concentration (wt. %) | 63 | — | 53 |
| Product-Containing | Acid Value (mg/g) |  |  |  |
| Reaction Solution | Measured Value[2] | 444 | — | 550 |
|  | Theoretical Value | 394[4] | 394[4] | 525.8[8] |
| Mixture To Be | Intermediate-Product-Containing | 330 | 497 | 425 |
| Hydrolyzed | Reaction Solution (g) |  |  |  |
|  | Water    (g) | 14.76 | 19.8 | 20 |
|  |            (mol) | 0.82 | 1.1 | 1.1 |
| Hydrolysis Conditions | Temperature (° C.) | 70-80 | 70-95 | 70-80 |
|  | Time (min.) | 30 | 30 | 30 |
| Hydrolyzed Reaction | Solid Concentration (wt. %) | 64 | 61.5 | 55 |
| Solution | Acid Value (mg/g) |  |  |  |
|  | Measured Value[2] | 795.3 | 760 | 959.1 |
|  | Theoretical Value | 741.7[5] | 741.7[5] | 969.7[9] |
|  | Refractive Index | — | 1.4806 | — |

|  |  | No. | |
|---|---|---|---|
|  |  | Example 4 | Example 5 |
| Reaction Mixture | (Meth)acrylamide Monomer | Acrylamide | TBAS[10] |
|  |  | 71 g | 207 g |
|  |  | (1 mole) | (1 mole) |
|  | Phosphoric Anhydride | 156 g | 78 g |
|  |  | (1.1 mole) | (0.55 mole) |
|  | Polymerization Inhibitor[1] | 1.0 g | 1.0 g |
|  | Solvent | DMAA[6] | DMAA[6] |
|  |  | 198 g | 200 g |
|  |  | (2.0 mole) | (2.02 mole) |
| Addition of | Adding Time (hrs.) | 3 | 2 |
| Phosphoric Anhydride | Number of installments | 8 | 2 |
| Reaction Conditions | Temperature (° C.) | 70-95 | 70-95 |
|  | Stirring (rpm) | 300-400 | 300-400 |
| Aging Conditions |  | 80° C. × 2 hrs. | 70-95° C. × 1 hr. |
| Intermediate | Solid Concentration (wt. %) | — | — |
| Product-Containing | Acid Value (mg/g) |  |  |
| Reaction Solution | Measured Value[2] | — | 404.0 |
|  | Theoretical Value | 525.8[8] | 402.9[11] |
| Mixture To Be | Intermediate-Product-Containing | 426 | 486 |
| Hydrolyzed | Reaction Solution (g) |  |  |
|  | Water    (g) | 19.8 | 9.9 |
|  |            (mol) | 1.1 | 0.55 |
| Hydrolysis Conditions | Temperature (° C.) | 70-95 | 70-90 |
|  | TIME (min.) | 30 | 30 |
| Hydrolyzed Reaction | Solid Concentration (wt. %) | 55 | 58 |
| Solution | Acid Value (mg/g) |  |  |
|  | Measured Value[2] | 975.6 | 594.6 |
|  | Theoretical Value | 969.7[9] | 585.4 |
|  | Refractive Index | 1.4840 | 1.4868 |

|  |  | No. | |
|---|---|---|---|
|  |  | Example 6 | Example 7 |
| Reaction Mixture | (Meth)acrylamide Monomer | Acrylamide | Acrylamide |
|  |  | 55.42 g | 56.8 g |
|  |  | (0.78 mole) | (0.8 mole) |
|  | Phosphoric Anhydride | 62.24 g | 85.2 g |
|  |  | (0.44 mole) | (0.6 mole) |
|  | Polymerization Inhibitor[1] | 0.5 g | 0.8 g |
|  | Solvent | DMAA + Phosphonic | DMAA + Phosphonic |
|  |  | TBAS[12] | TBAS[15] |
|  |  | 100 g | 130 g |
| Addition of | Adding Time (hrs.) | 3 | 3 |
| Phosphoric Anhydride | Number of Installments | 5 | 8 |
| Reaction Conditions | Temperature (° C.) | 70-95 | 70-95 |
|  | Stirring (rpm) | 300-400 | 300-400 |
| Aging Conditions |  | 80° C. × 2 hrs. | 80° C. × 2 hrs. |
| Intermediate | Solid Concentration (wt. %) | — | — |
| Product-Containing | Acid Value (mg/g) |  |  |

TABLE 3-continued

| | | | |
|---|---|---|---|
| Reaction Solution | Measured Value[2] | — | — |
| | Theoretical Value | — | — |
| Mixture To Be Hydrolyzed | Intermediate-Product-Containing Reaction Solution (g) | 218 | 272.5 |
| | Water (g) | 10 | 18 |
| | (mol) | 0.56 | 1 |
| Hydrolysis Conditions | Temperature (° C.) | 70-95 | 70-95 |
| | Time (min.) | 30 | 30 |
| Hydrolyzed Reaction Solution | Solid Concentration (wt. %) | 80.7 | 76.2 |
| | Acid Value (mg/g) | | |
| | Measured Value[2] | 700[13] | 802[13] |
| | Theoretical Value | 719.5[14] | 788.2[14] |
| | Refractive Index | 1.4876 | 1.4814 |

Note:
[1]Hydroquinone monomethyl ether.
[2]Expressed on a solid basis, measured using a 1-N aqueous KOH solution with titration termination at pH of 10.3.
[3]Dimethylformamide.
[4]The theoretical acid value of pyrophosphonic diacrylamide.
[5]The theoretical acid value of phosphonic acrylamide.
[6]N,N-dimethyl acrylamide.
[7]N,N-dimethylacetamide.
[8]The theoretical acid value of a compound having pyrophosphoric acid N,N-linked to acrylamide, or a compound having two acrylamide molecules bond to dipyrophosphoric acid.
[9]The theoretical acid value of N,N-diphosphonic acrylamide.
[10]t-Butyl acrylamide sulfonic acid.
[11]The theoretical acid value of di(t-butyl acrylamide sulfonic acid) pyrophosphonic acid.
[12]The reaction solution prepared in Example 5 [a solution of phosphonic-group-containing t-butyl acrylamide sulfonic acid in DMAA (concentration: 58% by mass)].
[13]The acid value of the composition.
[14]Average theoretical acid value.
[15]118 g of the reaction solution prepared in Example 5 [a solution of phosphonic-group-containing t-butyl acrylamide sulfonic acid in DMAA (concentration: 58% by mass)] + 12 g of DMAA.

EXAMPLE 8

1.5 g of hexamethylenediol diacrylate (available from Nippon Kayaku Co., Ltd.), and a photopolymerization initiator [IRUGACURE 651 (2,2-dimethoxy-1,2-diphenylethane-1-on available from Ciba Specialty Chemicals)+IRUGACURE 500 (1-hydroxycyclohexyl phenyl ketone, benzophenone available from Ciba Specialty Chemicals)=0.75 (g)+0.75 (g)] were dissolved in 97 g of the solution of phosphonic acrylamide in DMAA (solid concentration: 61.5% by mass) obtained in Example 2, and polyoxyethylene glycol mono (perfluorooctyl sulfoamide ethyl ether) (Megafac 142-D available from Dainippon Ink And Chemicals, Inc.) was added in an amount of 1% by mass per the entire composition. The resultant composition was sandwiched by two flat glass plates each having a fluororesin film attached (see FIGS. 1 and 2). Using a high-voltage mercury lamp (TOSCURE 400 HC-0411, available from Toshiba Denzai K.K.), the composition was irradiated with ultraviolet rays with intensity of 100 mW/cm$^2$ at an irradiation distance of 10 cm from both sides each for 60 seconds, to produce a membrane by photopolymerization. The surface intrinsic resistivity of the resultant membrane was measured under the conditions of RH 50% and 20° C., using a surface intrinsic resistivity meter SME-8310 available from To a Denpa Kogyo K.K. The same surface-intrinsic-resistivity-measuring method was also used below. The results are shown in Table 4.

EXAMPLE 9

A polymer membrane was produced in the same manner as in Example 8, except for adding 2.5 g of hexamethylenediol diacrylate, and 2.5 g of a photopolymerization initiator [IRUGACURE 651+IRUGACURE 500=1.25 (g)+1.25 (g)] to 95 g of the solution of phosphonic acrylamide in DMAA obtained in Example 2 (solid concentration: 61.5% by mass). The surface intrinsic resistivity of the resultant membrane was measured in the same manner as in Example 8. The results are shown in Table 4.

EXAMPLE 10

A polymer membrane was produced in the same manner as in Example 8 except for adding 1.5 g of DMAA and 1.5 g of a photopolymerization initiator [IRUGACURE 651+IRUGACURE 500=0.75 (g)+0.75 (g)] to 97 g of the solution of N,N-diphosphonic acrylamide in DMAA obtained in Example 4. The surface intrinsic resistivity of the resultant membrane was measured under the conditions of RH 40% and 20° C. The results are shown in Table 4.

EXAMPLE 11

A polymer membrane was produced in the same manner as in Example 8 except for adding 360 g of a composition comprising acryloyloxyethyl phosphate (molecular weight: 196) and di(acryloyloxyethyl)phosphate (molecular weight: 294) at a molar ratio of 1:1 (Phosmer 2A available from UNI-CHEMICAL CO. LTD.), 2.5 g of hexamethylenediol diacrylate, and 2.5 g of a photopolymerization initiator [IRUGACURE 651+IRUGACURE 500=1.25 (g)+1.25 (g)] to 65 g of the solution of N,N-diphosphonic acrylamide in DMAA obtained in Example 4. The surface intrinsic resistivity of the resultant membrane was measured in the same manner as in Example 10. The results are shown in Table 4.

TABLE 4

| | | No. | | | |
|---|---|---|---|---|---|
| | | Example 8 | Example 9 | Example 10 | Example 11 |
| Formulation (g) | Phosphonic Acrylamide | 59.7 | 58.4 | — | — |
| | N,N-Diphosphonic Acrylamide | — | — | 53.35 | 35.75 |
| | Hexamethylenediol Diacrylate | 1.5 | 2.5 | — | — |
| | Phosmer 2A[(1)] | — | — | — | 360 |
| | DMAA[(2)] | 37.3 | 36.6 | 45.15 | 29.25 |
| Photopolymerization Initiator[(3)] (g) | | 1.5 | 2.5 | 1.5 | 2.5 |
| Release Agent[(4)] (% by Mass per Entire Composition) | | 1 | 1 | 1 | 1 |
| Surface Intrinsic Resistivity ($\Omega \cdot cm$) | | $5.28 \times 10^{5[(5)]}$ | $6.34 \times 10^{5[(5)]}$ | $1.01 \times 10^{6[(6)]}$ | $4.36 \times 10^{5[(6)]}$ |

Note:
[(1)]A composition comprising acryloyloxyethyl phosphate (molecular weight: 196) and di(acryloyloxyethyl) phosphate (molecular weight: 294) at a molar ratio of 1:1.
[(2)]N,N-dimethyl acrylamide.
[(3)]IRUGACURE 651/IRUGACURE 500 = 1/1 by mass, available from Ciba Specialty Chemicals.
[(4)]Polyoxyethylene glycol mono(perfluorooctyl sulfoamide ethyl ether) (Megafac 142-D available from Dainippon Ink And Chemicals, Inc.).
[(5)]RH 50% and 20° C.
[(6)]RH 40% and 20° C.

EXAMPLE 12

44.5 g of the (poly)phosphonic acrylamide composition solution (solid concentration: 64% by mass) prepared in Example 1, 77.0 g of 2-propyl alcohol, and 154.0 g of ion-exchanged water were charged into the same automatic synthesis reactor as in Example 1, and heated to 65° C. while stirring at 140-150 rpm and introducing a nitrogen gas. After confirming that the inside-reactor temperature reached 65° C., a solution of 0.3 g of ammonium persulphate in 5.0 g of ion-exchanged water was added. At this time, slight heat generation occurred, confirming that polymerization started. Each time 2 and 3 hours after the initial addition of the catalyst, a solution of 0.1 g of ammonium persulphate in 5.0 g of ion-exchanged water was added. The remaining monomer was polymerized by keeping at 65° C. for 1 hour, to obtain a phosphonic-group-containing acrylamide polymer solution with a solid concentration of 11.5% by mass. The resultant polymer solution had a viscosity of 91 mPa·s at 20° C.

EXAMPLES 13, 14

The 11.5-%-by-mass solution of (poly)phosphonic-group-containing acrylamide polymer obtained in Example 12, and a 10-%-by-mass aqueous solution of polyvinyl alcohol (EXCEVAL RS-2113, saponification degree: 97.5-99.0, available from Kuraray Chemical Co., Ltd.) were mixed according to the solid formulations shown in Table 5. The resultant polymer solution was cast on a polypropylene-film-made vessel (bottom surface; 20 cm×20 cm), and dried at 50° C. for 12 hours in an air-flowing drier. The resultant membrane was peeled by a spatula, and heat-treated at 130° C. for 3 minutes in a high-temperature-air-flowing drier to obtain a 100-μm-thick conductive resin film.

EXAMPLES 15, 16

Conductive resin films were produced in the same manner as in Example 13, except that polymer solutions were prepared by mixing the 11.5-%-by-mass solution of a (poly) phosphonic-group-containing acrylamide polymer obtained in Example 12, a 10-%-by-mass aqueous polyvinyl alcohol solution, and a 80-%-by-mass aqueous solution of trimethoxymethyl melamine (Sumitex Resin M-3 available from Sumitomo Chemical Co., Ltd.) according to the solid formulations shown in Table 5.

COMPARATIVE EXAMPLE 1

A conductive resin film was produced in the same manner as in Example 13 except for using only a 110-%-by-mass aqueous polyvinyl alcohol solution.

COMPARATIVE EXAMPLE 2

A conductive resin film was produced in the same manner as in Example 13 except for preparing a polymer solution by mixing a 10-%-by-mass aqueous polyvinyl alcohol solution and a 80-%-by-mass aqueous trimethoxymethyl melamine solution according to the solid formulation shown in Table 6.

The properties of the conductive resin films produced in Examples 13-16 and Comparative Examples 1, 2 were measured according to the following methods. The results are shown in Tables 5 and 6.

(1) Appearance: Transparency observed by the naked eye was evaluated by the following standards:
Excellent: "Colorless transparent," and
Good: "Slightly opaque."

(2) Tackiness: After each conductive resin film was left to stand under the conditions of a temperature of 20° C. and a relative humidity of 50% for half a day or longer, it was touched with a finger and evaluated by its feeling according to the following standards:
Excellent: "Not tacky," and
Good: "slightly tacky."

Figure 3A:
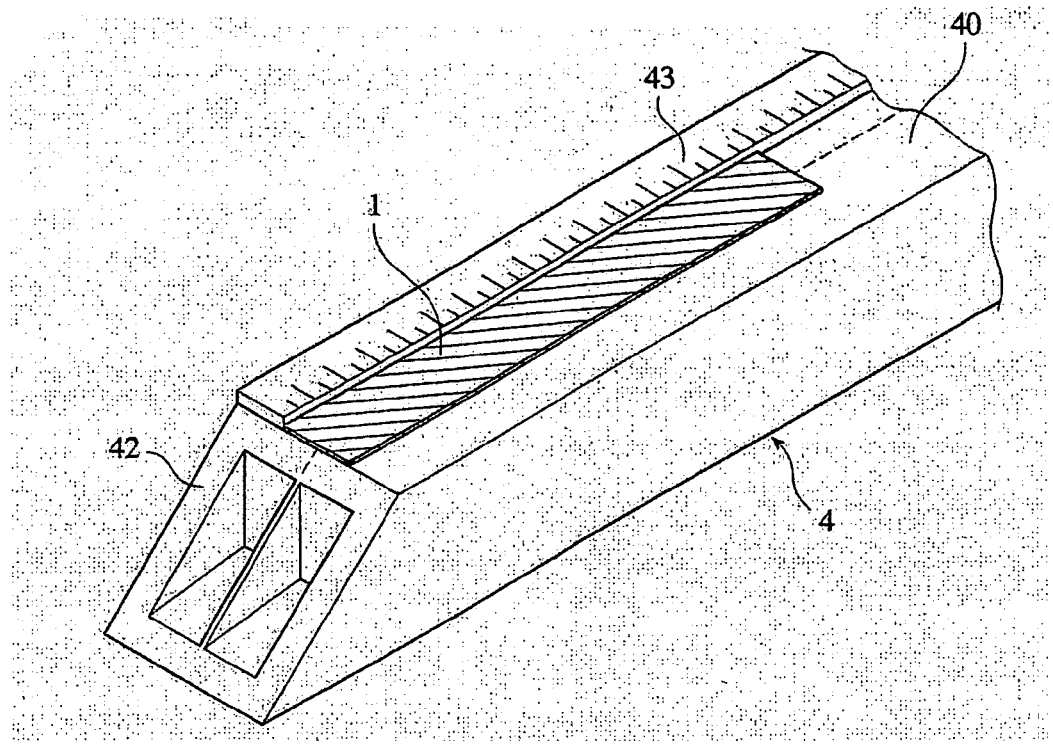
FIG. 3(a) is a partial perspective view showing a test piece placed on a softness tester.
Figure 3B:
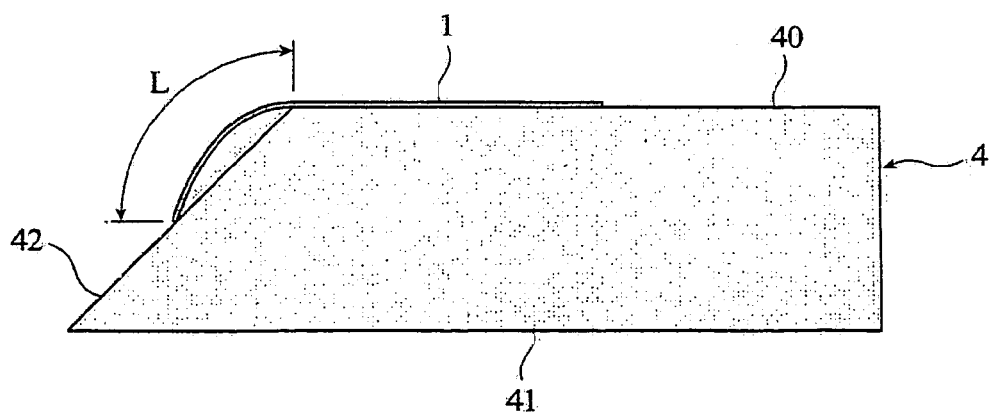
FIG. 3(b) is a schematic side view showing a test piece moving along a slanting surface on the softness tester.

(3) Softness: Evaluated by a cantilever method according to JIS-L-1096, using a tester used shown in FIG. 3. The tester 4 had an upper surface 40 and a lower surface 41 both horizontal, with a 45-degree slanting end surface 42. A rectangular test piece 1 of 2 cm×15 cm was cut out and placed on the tester 4 with one end of the test piece 1 along the base line of a scale 43 on the upper surface 40 as shown in FIG. 3(a). The test piece 1 was then caused to slowly slide along the slanting surface 42. As shown in FIG. 3(b), when one end of the test piece 1 came to contact with the slanting surface 42, the position of the other end of the test piece 1 was read by the scale 43, thereby measuring the length L (mm) by which the test piece 1 moved. The evaluation standards are as follows:

Excellent: Length L was 3 cm or less, and

Good: Length L was more than 3 cm and 6 cm or less.

(4) Water resistance: A strip sample of 1 cm×4 cm was cut out, and its area (length×width) was used as a reference. The cutout sample was immersed in water at room temperature, and taken out after 30 minutes and 2 days, respectively, to measure the length and width of the sample to calculate the area. Thus, a swelling ratio relative to the reference area was determined. Also, the appearance after 2 days was observed by the naked eye and evaluated by the following standards:

Excellent: Colorless transparent, and

Good: Slightly opaque.

(6) Surface intrinsic resistivity: measured under the conditions of RH 50%/20° C., RH 65%/19° C., and RH 73%/19° C., using a surface intrinsic resistivity meter (SME-8310 available from To a Denpa Kogyo K.K.).

TABLE 5

| | | No. | | | |
|---|---|---|---|---|---|
| | | Example 13 | Example 14 | Example 15 | Example 16 |
| Formulation (Parts by Mass) | (Poly)Phosphonic-Group-Containing Acrylamide Polymer | 20 | 40 | 18.2 | 36.4 |
| | Polyvinyl Alcohol[(1)] | 80 | 60 | 72.7 | 54.5 |
| | Trimethoxymethyl Melamine[(2)] | 0 | 0 | 9.1 | 9.1 |
| Conditions of Film | Appearance | Good | Good | Good | Good |
| | Tackiness | Good | Good | Good | Good |
| | Softness | Excellent | Excellent | Good | Excellent |
| Water Resistance | Appearance After 2 Days | Good | Good | Fair | Fair |
| | Swelling Ratio (%) After 30 Minutes | +69 | +59 | +50 | +63 |
| | After 2 Days | +72 | +59 | +66 | +66 |
| Methanol Resistance | Appearance After 2 Days | Good | Good | Good | Good |
| | Swelling Ratio (%) After 30 Minutes | +3 | +5 | +13 | +3 |
| | After 2 Days | +3 | +5 | +13 | +3 |
| Surface Intrinsic Resistivity ($\Omega \cdot$ cm) | RH 50%/20° C. | $2.4 \times 10^5$ | $9.6 \times 10^4$ | $8.8 \times 10^6$ | $8.5 \times 10^4$ |
| | RH 65%/19° C. | $8.8 \times 10^4$ | $2.8 \times 10^4$ | $3.2 \times 10^6$ | $8.3 \times 10^4$ |
| | RH 73%/19° C. | $1.1 \times 10^5$ | $2.1 \times 10^4$ | $7.9 \times 10^4$ | $4.1 \times 10^4$ |

Note:
[(1)]EXCEVAL RS-2113, saponification degree: 97.5-99.0, available from Kuraray Chemical Co., Ltd.
[(2)]Sumitex Resin M-3 available from Sumitomo Chemical Co., Ltd.

TABLE 6

| | | No. | |
|---|---|---|---|
| | | Comparative Example 1 | Comparative Example 2 |
| Formulation (Parts by Mass) | Polyvinyl Alcohol[(1)] | 100 | 90.9 |
| | Trimethoxymethyl Melamine[(2)] | 0 | 9.1 |
| Conditions of Film | Appearance | Excellent | Excellent |
| | Tackiness | Excellent | Excellent |
| | Softness | Excellent | Good |
| Water Resistance | Appearance After 2 Days | Excellent | Good |
| | Swelling Ratio (%) After 30 Minutes | +20 | +20 |
| | After 2 Days | +35 | +20 |
| Methanol Resistance | Appearance after 2 days | Excellent | Good |
| | Swelling Ratio (%) After 30 Minutes | +5 | +7 |
| | After 2 Days | +7 | +7 |
| Surface Intrinsic Resistivity ($\Omega \cdot$ cm) | RH 50%/22° C. | $9.0 \times 10^{13}$ | $2.3 \times 10^{12}$ |
| | RH 65%/19° C. | $9.0 \times 10^{11}$ | $1.2 \times 10^{12}$ |
| | RH 75%/19° C. | $7.1 \times 10^9$ | $1.6 \times 10^9$ | and taken out after 30 minutes and 2 days, respectively, to measure the length and width of the sample to calculate the area. Thus, a swelling ratio relative to the reference area was determined. Also, the appearance after 2 days was observed by the naked eye and evaluated by the following standards:

Excellent: Colorless transparent,

Good: Slightly opaque, and

Fair: Whitened or clouded.

(5) Methanol resistance: A strip sample of 1 cm×4 cm was cut out to measure its area, which was used as a reference. The cutout sample was immersed in methanol at room temperature, and taken out after 30 minutes and 2 days, respectively, to measure the length and width of the sample to calculate the As shown in Table 4, the films of Examples 8-11 exhibited surface intrinsic resistivity of $10^5$-$10^7 \Omega \cdot$cm under the measurement conditions of RH 40%/20° C. or RH 50%/20° C. As shown in Table 5, the films of Examples 13-16 had excellent transparency and softness, with no or little, if necessary, tackiness. Although the films of Examples 13-16 suffered swelling and slight whitening or clouding by immersion in water or methanol, they were not dissolved, causing no practical problems. The surface intrinsic resistivity of the films of Examples 13-16 was $10^4$-$10^7 \Omega \cdot$cm at RH 50%/20° C. and RH 65%/19° C., and $10^4$-$10^6$ $\Omega \cdot$cm at RH 73%/19° C. Because the films of Comparative Examples 1 and 2 did not contain a (poly)phosphonic-group-containing acrylamide polymer, as shown in Table 6, they exhibited higher surface intrinsic resistivity than the conductive resin films of Examples 8-11 and 13-16 by substantially 4-8 powers. The comparison of Examples 13-16 and Comparative Examples 1 and 2 revealed that polyvinyl alcohol could be provided with remarkably reduced surface intrinsic resistivity merely by adding a (poly) phosphonic-group-containing acrylamide polymer in an amount of about 20% by mass per the entire resin composition.

EXAMPLES 17-23

(1) Preparation of Phosphatized Glycerol Dimethacrylate 342 g (1.5 mole) of glycerol dimethacrylate [Blemmer GMR-H, hydroxyl equivalent: 239 (analyzed value), available from NOF Corp.] was charged into the same automatic synthesis reactor as in Example 1, and heated to 60° C. After confirming that the inside-reactor temperature reached 60° C., 117 g (0.825 mole) of phosphoric anhydride was introduced with six installments with substantially equal intervals over 6 hours through a powder inlet. During adding phosphoric anhydride, the inside-reactor temperature was kept within 70-90° C. while stirring at 420 rpm. After all phosphoric anhydride was added, an aging reaction was conducted at 80° C. for 2 hours.

The resultant solution was filtered by a metal net (100 mesh) to remove impurities such as a trace amount of polyphosphoric acid, etc. The filtered solution was returned to the reaction vessel, and 22 g (1.22 mole) of water was added thereto over 1 hour through a dropping funnel while heating at 80-85° C. and stirring at 420 rpm. Thereafter, an aging reaction was conducted at that temperature for 2 hours. The hydrolyzed reaction solution had a color number of 3 and a refractive index of 1.4745 at 20° C. Because the acid value measured on 1 g of the hydrolyzed solution was 351 mg/g, it was confirmed that phosphatized glycerol dimethacrylate (theoretical acid value: 363.6 mg/g), which is called "PGDM" unless otherwise mentioned, was synthesized.

(2) Production of Polymer Electrolyte Membrane

The solution of phosphonic acrylamide in DMAA (solid concentration: 61.5% by mass) obtained in Example 2, the solution of N,N-diphosphonic acrylamide in DMAA (solid concentration: 55% by mass) obtained in Example 4, acid phosphoxyethyl methacrylate (Phosmer M available from UNI-CHEMICAL CO. LTD.), acid phosphoxypolyoxypropylene glycol methacrylate (Phosmer PP available from UNI-CHEMICAL CO. LTD.), PGDM prepared in the above step (1), methacrylic acid, acrylonitrile, a liquid butadiene oligomer end-modified with acrylics (NISSO-PB TE-2000 available from Nippon Soda Co., Ltd.), butyralized polyvinyl alcohol (S-LEC B BL-1, hydroxyl group: 36 mol %, acetyl group: 3 mol % or less, butyralization degree: 63±3 mol %, available from Sekisui Chemical Co., Ltd.), and vinyl-chloride-unit-containing polyvinyl alcohol (SOLBIN TA5R, vinyl chloride unit: 87% by mass, vinyl acetate unit: 1% by mass, vinyl alcohol unit: 12% by mass, available from Nissin Chemical Industry Co., Ltd.) were mixed to prepare compositions having the formulations shown in Table 7.

A polymerization initiator mixture comprising IRUGA-CURE 651 (2,2-dimethoxy-1,2-diphenylethane-1-on available from Ciba Specialty Chemicals), IRUGACURE 500 (1-hydroxycyclohexyl phenyl ketone, benzophenone), and benzoyl peroxide (BPO) at a mass ratio of 1/1/0.1 (IRUGA-CURE 651/IRUGACURE 500/BPO) was added to the resultant composition in the proportion (per the composition) shown in Table 7.

The above polymerization-initiator-containing composition was dropped onto a diagonal center of a square glass plate of 20 cm each lined with a polyethylene film, a peripheral portion of which was provided with a 100-μm-thick spacer tape. A glass plate lined with a polyethylene film was attached to the composition to sandwich it by two flat glass plates (see FIGS. 1 and 2). In this state, the composition was photopolymerized by irradiating the composition on both sides with ultraviolet rays for 10 minutes each by a high-voltage mercury lamp (400 W) at an irradiation distance of 20 cm. Further, using an electronic oven at 500 W, it was heat-treated for 2 minutes to produce a 100-μm-thick polymer electrolyte membrane. The resultant membrane was transparent with excellent uniformity.

EXAMPLES 24-30

The solution of phosphonic-group-containing t-butyl acrylamide sulfonic acid in DMAA (solid concentration: 58% by mass) obtained in Example 5, the solution of a composition (45.5% by mass of phosphonic acrylamide+9.7% by mass of N,N-diphosphonic acrylamide+25.5% by mass of phosphonic-group-containing t-butyl acrylamide sulfonic acid) in DMAA obtained in Example 6, the solution of a composition (20.7% by mass of phosphonic acrylamide+31.8% by mass of N,N-diphosphonic acrylamide+23.7% by mass of phosphonic-group-containing t-butyl acrylamide sulfonic acid) in DMAA obtained in Example 7, acid phosphoxyethyl methacrylate (Phosmer M), acid phosphoxypolyoxypropylene glycol methacrylate (Phosmer PP), PGDM prepared in the same manner as in Example 17, methacrylic acid, acrylonitrile, a liquid butadiene oligomer end-modified with acrylics (NISSO-PB TE-2000), butyralized polyvinyl alcohol (S-LEC B BL-1), and vinyl-chloride-unit-containing polyvinyl alcohol (SOLBIN TA5R) were mixed to prepare compositions having the formulations shown in Table 8. The resultant compositions were mixed with a polymerization initiator mixture having the same composition as in Example 17 in the proportion shown in Table 8. The compositions were formed into polymer electrolyte membranes in the same manner as in Example 17. The resultant membranes were transparent with excellent uniformity.

The properties (water resistance, methanol resistance, hot water resistance, surface intrinsic resistivity and proton conductivity) of the polymer electrolyte membranes produced in Examples 17-30 were measured. The methods for measuring water resistance and methanol resistance were the same as described above. The methods for measuring hot water resistance, surface intrinsic resistivity and proton conductivity were as follows: The results are shown in Tables 7 and 8.

(1) Hot water resistance: A strip sample of 1 cm×4 cm was cut out to measure its area as a reference. The cutout sample was immersed in hot water at 80° C., and taken out after 2 hours to measure the length and width of the sample to calculate the area. Thus, a swelling ratio relative to the reference area was determined.

(2) Surface intrinsic resistivity: Measured under the conditions of RH 60% and 15° C. using a surface intrinsic resistivity meter (SME-8310 available from To a Denpa Kogyo K.K.).

(3) Proton conductivity: Measured using a complex impedance method. A rectangular sample of 3 cm×1 cm was cut out, and placed in an open impedance cell. This cell was charged into a constant-temperature, constant-humidity chamber to conduct impedance measurement at a relative humidity of 90% in a temperature range of 35-80° C. The measured data were analyzed to obtain plane complex impedance, which was treated on a Cole-Cole plot to determine the conductivity of the sample from its resistivity.

TABLE 7

| | | Example 17 | Example 18 | Example 19 |
|---|---|---|---|---|
| Formulation (Parts by Mass) | Phosphonic Acrylamide | 15.8 | 20.8 | 13.9 |
| | N,N-Diphosphonic Acrylamide | — | — | — |
| | Phosmer M[(1)] | 25.6 | 33.9 | 7.0 |
| | Phosmer PP[(2)] | — | — | — |
| | PGDM[(3)] | 3.4 | 2.3 | 0.5 |
| | Methacrylic Acid | — | 5.6 | — |
| | Acrylonitrile | 32.5 | 16.5 | 34.8 |
| | DMAA[(4)] | 9.9 | 13.1 | 8.6 |
| | Acrylic-Modified Liquid Butadiene Oligomer[(5)] | — | — | — |
| | Butyralized Polyvinyl Alcohol[(6)] | 12.8 | 5.9 | 35.2 |
| | Vinyl-Chloride-Unit-Containing Polyvinyl Alcohol[(7)] | — | 1.9 | — |
| Photopolymerization Initiator[(8)] (% by mass per Composition) | | 3.7 | 2.5 | 0.56 |
| Water Resistance (%) (Swelling Ratio at Room Temperature After 30 min.) | | 0 | +11 | 0 |
| Methanol Resistance (%) (Swelling Ratio at Room Temperature After 30 min.) | | +38 | +21 | +1 |
| Hot Water Resistance (%) (Swelling Ratio at 80° C. After 2 Hours) | | 0 | +21 | −12 |
| Surface Intrinsic Resistivity (Ω · cm) (15° C./RH 60%) | | $3.05 \times 10^{4}$ | $2.24 \times 10^{5}$ | $1.94 \times 10^{6}$ |
| Proton Conductivity (S · cm$^{-1}$) | 35° C./RH 90% | $1.2 \times 10^{-3}$ | — | $8.2 \times 10^{-4}$ |
| | 50° C./RH 90% | — | — | $1.3 \times 10^{-3}$ |
| | 65° C./RH 90% | $4.1 \times 10^{-3}$ | $4.4 \times 10^{-3}$ | $2.6 \times 10^{-3}$ |
| | 80° C./RH 90% | $7.2 \times 10^{-3}$ | $3.2 \times 10^{-3}$ | $5.7 \times 10^{-3}$ |

| | | Example 20 | Example 21 | Example 22 |
|---|---|---|---|---|
| Formulation (Parts by Mass) | Phosphonic Acrylamide | 48.6 | — | — |
| | N,N-Diphosphonic Acrylamide | — | 18.0 | 18.7 |
| | Phosmer M[(1)] | — | — | 33.9 |
| | Phosmer PP[(2)] | 1.2 | 16.3 | — |
| | PGDM[(3)] | 0.4 | 0.9 | 2.2 |
| | Methacrylic Acid | — | — | 5.6 |
| | Acrylonitrile | 7.0 | 34.0 | 16.5 |
| | DMAA[(4)] | 30.4 | 14.7 | 15.3 |
| | Acrylic-Modified Liquid Butadiene Oligomer[(5)] | 12.4 | — | — |
| | Butyralized Polyvinyl Alcohol[(6)] | — | 16.1 | 5.9 |
| | Vinyl-Chloride-Unit-Containing Polyvinyl Alcohol[(7)] | — | — | 1.9 |
| Photopolymerization Initiator[(8)] (% by mass per Composition) | | 0.45 | 0.95 | 2.5 |
| Water Resistance (%) (Swelling Ratio at Room Temperature After 30 min.) | | +61 | +4 | +16 |
| Methanol Resistance (%) (Swelling Ratio at Room Temperature After 30 min.) | | +27 | +50 | +27 |
| Hot Water Resistance (%) (Swelling Ratio at 80° C. After 2 Hours) | | +65 | −1 | +17 |
| Surface Intrinsic Resistivity (Ω · cm) (15° C./RH 60%) | | $5.55 \times 10^{4}$ | $2.56 \times 10^{5}$ | $8.14 \times 10^{5}$ |
| Proton Conductivity (S · cm$^{-1}$) | 35° C./RH 90% | — | $1.8 \times 10^{-3}$ | $2.7 \times 10^{-2}$ |
| | 50° C./RH 90% | $3.8 \times 10^{-2}$ | $4.4 \times 10^{-3}$ | $3.4 \times 10^{-2}$ |
| | 65° C./RH 90% | $3.1 \times 10^{-2}$ | $5.3 \times 10^{-3}$ | $4.8 \times 10^{-3}$ |
| | 80° C./RH 90% | $2.1 \times 10^{-2}$ | $5.4 \times 10^{-3}$ | $2.9 \times 10^{-3}$ |

| | | Example 23 |
|---|---|---|
| Formulation (Parts by Mass) | Phosphonic Acrylamide | — |
| | N,N-Diphosphonic Acrylamide | 14.1 |
| | Phosmer M[(1)] | — |
| | Phosmer PP[(2)] | 25.7 |
| | PGDM[(3)] | 3.4 |
| | Methacrylic Acid | — |
| | Acrylonitrile | 32.5 |
| | DMAA[(4)] | 11.5 |
| | Acrylic-Modified Liquid Butadiene Oligomer[(5)] | — |
| | Butyralized Polyvinyl Alcohol[(6)] | 12.8 |
| | Vinyl-Chloride-Unit-Containing | — |

TABLE 7-continued

| | | |
|---|---|---|
| Polyvinyl Alcohol[7] | | |
| Photopolymerization Initiator[8] (% by mass per Composition) | | 3.7 |
| Water Resistance (%) (Swelling Ratio at Room Temperature After 30 min.) | | +3 |
| Methanol Resistance (%) (Swelling Ratio at Room Temperature After 30 min.) | | +29 |
| Hot Water Resistance (%) (Swelling Ratio at 80° C. After 2 Hours) | | +7 |
| Surface Intrinsic Resistivity ($\Omega \cdot cm$) (15° C./RH 60%) | | $2.14 \times 10^4$ |
| Proton Conductivity ($S \cdot cm^{-1}$) | 35° C./RH 90% | $1.4 \times 10^{-2}$ |
| | 50° C./RH 90% | $8.8 \times 10^{-3}$ |
| | 65° C./RH 90% | $3.4 \times 10^{-2}$ |
| | 80° C./RH 90% | $1.9 \times 10^{-2}$ |

Note:
[1]Acid phosphoxyethyl methacrylate (available from UNI-CHEMICAL CO. LTD.).
[2]Acid phosphoxypolyoxypropylene glycol methacrylate (available from UNI-CHEMICAL CO. LTD.).
[3]Phosphatized glycerol dimethacrylate.
[4]N,N-dimethyl acrylamide.
[5]NISSO-PB TE-2000 available from Nippon Soda Co., Ltd.
[6]S-LEC B BL-1 available from Sekisui Chemical Co., Ltd.
[7]SOLBIN TA5R (vinyl chloride unit: 87% by mass, vinyl acetate unit: 1% by mass, and vinyl alcohol unit: 12% by mass) available from Nissin Chemical Industry Co., Ltd.
[8]Comprising IRUGACURE 651 (2,2-dimethoxy-1,2-diphenyl-ethane-1-on available from Ciba Specialty Chemicals), IRUGACURE 500 (1-hydroxycyclohexyl phenyl ketone, benzophenone), and benzoyl peroxide (BPO) at a mass ratio of 1/1/0.1 (IRUGACURE 651/IRUGACURE 500/BPO).

TABLE 8

| | | No. | | |
|---|---|---|---|---|
| | | Example 24 | Example 25 | Example 26 |
| Formulation (Parts by Mass) | Phosphonic Acrylamide | 6.5 | 5.3 | 6.8 |
| | N,N-Diphosphonic Acrylamide | 10.0 | 8.1 | 10.4 |
| | Phosphonic-Acid-Group-Containing t-Butyl Acrylamide Sulfonic Acid | 7.4 | 6.1 | 7.8 |
| | Phosmer M[1] | 9.8 | 25.7 | — |
| | Phosmer PP[2] | — | — | 16.3 |
| | PGDM[3] | 0.7 | 3.4 | 0.7 |
| | Methacrylic Acid | — | — | — |
| | Acrylonitrile | 48.4 | 32.5 | 33.9 |
| | DMAA[4] | 7.4 | 6.1 | 7.8 |
| | Acrylic-Modified Liquid Butadiene Oligomer[5] | — | — | — |
| | Butyralized Polyvinyl Alcohol[6] | 9.8 | 12.8 | 16.3 |
| | Vinyl-Chloride-Unit-Containing Polyvinyl Alcohol[7] | — | — | — |
| Photopolymerization Initiator[8] (% by mass per Composition) | | 0.79 | 3.7 | 0.73 |
| Water Resistance (%) (Swelling Ratio at Room Temperature After 30 min.) | | +10 | +3 | +14 |
| Methanol Resistance (%) (Swelling Ratio at Room Temperature After 30 min.) | | +18 | +21 | +50 |
| Hot Water Resistance (%) (Swelling Ratio at 80° C. After 2 Hours) | | +22 | +28 | +38 |
| Surface Intrinsic Resistivity ($\Omega \cdot cm$) (15° C./RH 60%) | | $5.64 \times 10^4$ | $2.24 \times 10^5$ | $1.94 \times 10^6$ |
| Proton Conductivity ($S \cdot cm^{-1}$) | 35° C./RH 90% | $1.1 \times 10^{-3}$ | $2.7 \times 10^{-2}$ | $1.1 \times 10^{-2}$ |
| | 50° C./RH 90% | $1.5 \times 10^{-3}$ | $3.6 \times 10^{-2}$ | $2.3 \times 10^{-2}$ |
| | 65° C./RH 90% | $2.6 \times 10^{-3}$ | $4.7 \times 10^{-2}$ | $2.8 \times 10^{-2}$ |
| | 80° C./RH 90% | $5.2 \times 10^{-3}$ | $4.7 \times 10^{-2}$ | $2.3 \times 10^{-2}$ |

| | | No. | | |
|---|---|---|---|---|
| | | Example 27 | Example 28 | Example 29 |
| Formulation (Parts by Mass) | Phosphonic Acrylamide | — | — | 15.4 |
| | N,N-Diphosphonic Acrylamide | — | — | 3.3 |
| | Phosphonic-Acid-Group-Containing t-Butyl Acrylamide Sulfonic Acide | 14.9 | 19.7 | 8.6 |
| | Phosmer M[1] | 25.6 | 33.9 | 33.9 |
| | Phosmer PP[2] | — | — | — |
| | PGDM[3] | 3.4 | 2.3 | 2.3 |
| | Methacrylic Acid | — | 5.6 | 5.6 |
| | Acrylonitrile | 32.5 | 16.5 | 16.5 |

TABLE 8-continued

|  |  |  |  |  |
|---|---|---|---|---|
| | DMAA[4] | 10.8 | 14.2 | 6.6 |
| | Acrylic-Modified Liquid Butadiene Oligomer[5] | — | — | — |
| | Butyralized Polyvinyl Alcohol[6] | 12.8 | 5.9 | 5.9 |
| | Vinyl-Chloride-Unit-Containing Polyvinyl Alcohol[7] | — | 1.9 | 1.9 |
| Photopolymerization Initiator[8] (% by mass per Composition) | | 3.7 | 2.5 | 2.5 |
| Water Resistance (%) (Swelling Ratio at Room Temperature After 30 min.) | | +29 | +20 | +17 |
| Methanol Resistance (%) (Swelling Ratio at Room Temperature After 30 min.) | | +50 | +32 | +32 |
| Hot Water Resistance (%) (Swelling Ratio at 80° C. After 2 Hours) | | +47 | +27 | +18 |
| Surface Intrinsic Resistivity (Ω·cm) (15° C./RH 60%) | | $1.42 \times 10^5$ | $1.35 \times 10^5$ | $6.6 \times 10^4$ |
| Proton Conductivity ($S \cdot cm^{-1}$) | 35° C./RH 90% | $7.6 \times 10^{-3}$ | $2.2 \times 10^{-2}$ | $2.2 \times 10^{-2}$ |
| | 50° C./RH 90% | $2.2 \times 10^{-2}$ | $4.4 \times 10^{-2}$ | $2.4 \times 10^{-2}$ |
| | 65° C./RH 90% | $1.3 \times 10^{-2}$ | $7.4 \times 10^{-3}$ | $5.6 \times 10^{-3}$ |
| | 80° C./RH 90% | $3.4 \times 10^{-2}$ | $3.7 \times 10^{-3}$ | $4.1 \times 10^{-3}$ |

|  |  | No. Example 30 |
|---|---|---|
| Formulation (Parts by Mass) | Phosphonic Acrylamide | 11.7 |
| | N,N-Diphosphonic Acrylamide | 2.5 |
| | Phosphonic-Acid-Group-Containing t-Butyl Acrylamide Sulfonic Acid | 6.5 |
| | Phosmer M[1] | 25.6 |
| | Phosmer PP[2] | — |
| | PGDM[3] | 3.4 |
| | Methacrylic Acid | — |
| | Acrylonitrile | 32.5 |
| | DMAA[4] | 5.0 |
| | Acrylic-Modified Liquid Butadiene Oligomer[5] | — |
| | Butyralized Polyvinyl Alcohol[6] | 12.8 |
| | Vinyl-Chloride-Unit-Containing Polyvinyl Alcohol[7] | — |
| Photopolymerization Initiator[8] (% by mass per Composition) | | 3.7 |
| Water Resistance (%) (Swelling Ratio at Room Temperature After 30 min.) | | +17 |
| Methanol Resistance (%) (Swelling Ratio at Room Temperature After 30 min.) | | +61 |
| Hot Water Resistance (%) (Swelling Ratio at 80° C. After 2 Hours) | | +32 |
| Surface Intrinsic Resistivity (Ω·cm) (15° C./RH 60%) | | $\leq 1 \times 10^3$ |
| Proton Conductivity ($S \cdot cm^{-1}$) | 35° C./RH 90% | $1.3 \times 10^{-2}$ |
| | 50° C./RH 90% | $1.1 \times 10^{-2}$ |
| | 65° C./RH 90% | $2.0 \times 10^{-2}$ |
| | 80° C./RH 90% | $2.5 \times 10^{-2}$ |

Note:
[1]-[8] Same as in Table 7.

As shown in Tables 7 and 8, the polymer electrolyte membranes of Examples 17-30 suffered slight swelling by immersion in water, methanol and hot water, but they were not dissolved, causing no practical problems. The polymer electrolyte membranes of Examples 17-30 exhibited surface intrinsic resistivity of $1 \times 10^6$ Ω·cm or less at RH 60% and 15° C. The proton conductivity of the polymer electrolyte membranes of Examples 17-30 was on the level of $10^{-4}$-$10^{-2}$ S·cm$^{-1}$ under the conditions of a temperature of 35-80° C. and a relative humidity of 90%, which was good for polymer electrolytes having phosphorus acid groups as electrolytic groups.

EFFECT OF THE INVENTION

The phosphorus-acid-group-containing (meth)acrylamide of the present invention comprises a phosphorus acid group introduced into a (meth)acrylamide monomer, which may be N-substituted. Because a phosphorus-acid-group-containing (meth)acrylamide molecule is relatively small, its polymerization provides a polymer having a high electrolytic group density. Because the phosphorus-acid-group-containing (meth)acrylamide does not contain an ester group, its polymer has high hardness. Resins comprising this polymer as an indispensable component are useful for various applications such as conductive resins, solid polymer electrolytes, antistatic agents, anti-haze materials, paper/pulp modifiers, coating agents, etc. Particularly polymer electrolyte membranes made of this polymer have excellent proton conductivity derived from high-density phosphorus acid groups. Accordingly, the polymer electrolyte membranes of the present invention are suitable for electrolyte membranes for fuel cells, primary batteries and secondary batteries, display elements, various sensors, signal-transmitting media, solid capacitors, ion exchange membranes, etc. Particularly polymer electrolyte membranes comprising the cross-linked, phosphorus-acid-group-containing (meth)acrylamide polymer are expected to be used for high-power direct-methanol fuel cells (DMFCs).

Because the method of the present invention for producing a phosphorus-acid-group-containing (meth)acrylamide comprises (a) reacting a (meth)acrylamide monomer, which may be N-substituted, with phosphoric anhydride and/or phosphorus oxychloride, and hydrolyzing the resultant product, or (b) reacting a (meth)acrylamide monomer with at least one selected from the group consisting of phosphoric acid, pyrophosphoric acid and polyphosphoric acid, the phosphorus acid group can easily be introduced into the (meth)acrylamide monomer.

What is claimed is:

1. A phosphorus-acid-group-containing (meth)acrylamide comprising (meth)acrylamide represented by the following formula (1):

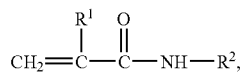

wherein $R^1$ is a hydrogen group or a methyl group, and $R^2$ is a hydrogen group or a substituted or unsubstituted hydrocarbon group, and a phosphorus acid group directly bonded to a nitrogen atom of an amide group in said (meth)acrylamide monomer.

2. The phosphorus-acid-group-containing (meth)acrylamide according to claim 1, comprising (poly)phosphonic (meth)acrylamide represented by the following formula (9):

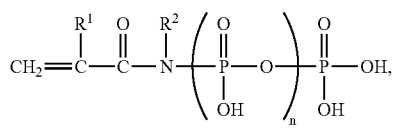

wherein $R^1$ is a hydrogen group or a methyl group, and $R^2$ is a hydrogen group or a substituted or unsubstituted hydrocarbon group, and n is an integer of 0-2, and/or N,N-diphosphonic(meth)acrylamide represented by the following formula (11):

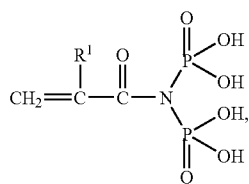

wherein $R^1$ is a hydrogen group or a methyl.

3. The phosphorus-acid-group-containing (meth)acrylamide according to claim 1, wherein said (meth)acrylamide is at least one selected from the group consisting of acrylamide, methacrylamide, and acrylamide alkane sulfonate represented by the following formula (2):

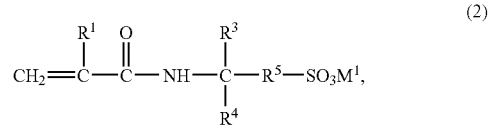

wherein $R^1$ is a hydrogen group or a methyl group, $R^3$ and $R^4$ are a hydrogen group or an alkyl group having 1-3 carbon atoms, $R^5$ is an alkylene group having 1-3 carbon atoms, and $M^1$ is a hydrogen group, a metal or a tertiary-amine group.

4. A phosphorus-acid-group-containing (meth)acrylamide polymer obtained by polymerizing a phosphorus-acid-group-containing (meth)acrylamide monomer comprising (meth)acrylamide represented by the following formula (1):

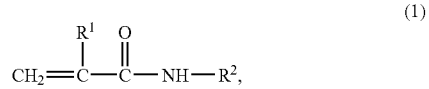

wherein $R^1$ is a hydrogen group or a methyl group, and $R^2$ is a hydrogen group or a substituted or unsubstituted hydrocarbon group, and a phosphorus acid group directly bonded to a nitrogen atom of an amide group in said (meth)acrylamide, said polymer having electric conductivity.

5. The electrically conductive, phosphorus-acid-group-containing (meth)acrylamide polymer according to claim 4, comprising as comonomers (a) an unsaturated compound containing one or more ethylenically unsaturated bonds and one or more acid groups in a molecule, and/or (b) an unsaturated compound containing one or more ethylenically unsaturated bonds but no acid group in a molecule.

6. The electrically conductive, phosphorus-acid-group-containing (meth)acrylamide polymer according to claim 4, wherein it is obtained by copolymerizing with (a) a phosphatized, alcoholic-hydroxyl-group-containing, unsaturated compound, and/or (b) a cross-linking agent having two or more ethylenically unsaturated bonds in a molecule.

7. A conductive resin comprising a phosphorus-acid-group-containing (meth)acrylamide polymer, which is a polymerization product of a phosphorus-acid-group-containing (meth)acrylamide monomer comprising (meth)acrylamide represented by the following formula (1):

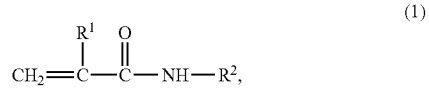

wherein $R^1$ is a hydrogen group or a methyl group, and $R^2$ is a hydrogen group or a substituted or unsubstituted hydrocarbon group, and a phosphorus acid group directly bonded to a nitrogen atom of an amide group in said (meth)acrylamide, wherein said polymer is electrically conductive.

8. The conductive resin according to claim 7, comprising at least one selected from the group consisting of unsaturated alcohol copolymers comprising an unsaturated alcohol unit and a vinyl halide unit and/or an aliphatic acid vinyl ester unit, partially acetalized unsaturated alcohol polymers, melamine resins, poly(meth)acrylonitrile, poly(meth)acrylate, polyacrylamide, poly(meth)acrylic acid, polyacetal, urethane resins, cellulose and its modified products, polystyrene, polyvinyl chloride, and polyvinyl acetate.

9. The conductive resin according to claim 7, wherein said (meth)acrylamide monomer is at least one selected from the group consisting of acrylamide, methacrylamide, and acrylamide alkane sulfonate represented by the following formula (2):

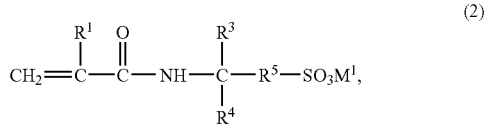

wherein $R^1$ is a hydrogen group or a methyl group, $R^3$ and $R^4$ are a hydrogen group or an alkyl group having 1-3 carbon atoms, $R^5$ is an alkylene group having 1-3 carbon atoms, $M^1$ is a hydrogen group, a metal or a tertiary-amine group.

10. The conductive resin according to claim 7, wherein said phosphorus-acid-group-containing (meth)acrylamide polymer comprises as comonomers (a) an unsaturated compound containing one or more ethylenically unsaturated bonds and one or more acid groups in a molecule, and/or (b) an unsaturated compound containing one or more ethylenically unsaturated bonds but no acid group in a molecule.

11. The conductive resin according to claim 10, wherein said unsaturated compound is a cross-linking agent having two or more ethylenically unsaturated bonds in a molecule.

12. A polymer electrolyte membrane comprising a polymer of a phosphorus-acid-group-containing (meth)acrylamide monomer, which comprises (meth)acrylamide represented by the following formula (1):

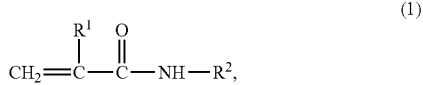

wherein $R^1$ is a hydrogen group or a methyl group, and $R^2$ is a hydrogen group or a substituted or unsubstituted hydrocarbon group, and a phosphorus acid group directly bonded to a nitrogen atom of an amide group in said (meth)acrylamide, wherein said membrane is electrically conductive.

13. The polymer electrolyte, electrically conductive membrane according to claim 12, wherein said (meth)acrylamide monomer is at least one selected from the group consisting of acrylamide, methacrylamide, and acrylamide alkane sulfonate represented by the following formula (2):

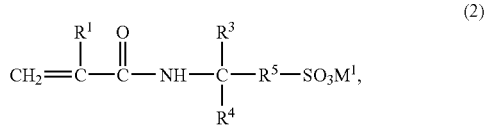

wherein $R^1$ is a hydrogen group or a methyl group, $R^3$ and $R^4$ are a hydrogen group or an alkyl group having 1-3 carbon atoms, $R^5$ is an alkylene group having 1-3 carbon atoms, $M^1$ is a hydrogen group, a metal or a tertiary-amine group.

14. The polymer electrolyte, electrically conductive membrane according to claim 12, wherein said polymer comprises as comonomers (a) an unsaturated compound containing one or more ethylenically unsaturated bonds and one or more acid groups in a molecule, and/or (b) an unsaturated compound containing one or more ethylenically unsaturated bonds but no acid group in a molecule.

15. The polymer electrolyte, electrically conductive membrane according to claim 12, wherein said unsaturated compound is a cross-linking agent having two or more ethylenically unsaturated bonds in a molecule.

16. A method for producing phosphorus-acid-group-containing (meth)acrylamide, comprising (a) reacting (meth)acrylamide represented by the following formula (I):

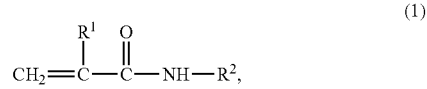

wherein $R^1$ is a hydrogen group or a methyl group, and $R^2$ is a hydrogen group or a substituted or unsubstituted hydrocarbon group, with phosphoric anhydride and/or phosphorus oxychloride, and hydrolyzing the resultant product, or (b) reacting said (meth)acrylamide with at least one selected from the group consisting of phosphoric acid, pyrophosphoric acid and polyphosphoric acid, in a solvent containing no active hydrogen and/or an acidic solvent, wherein a phosphorus acid group directly bonded to a nitrogen atom of an amide group in said (meth)acrylamide monomer.

17. The polymer electrolyte membrane having electric conductivity according to claim 12, wherein said electric conductivity is proton conductivity of $10^{-4}$-$10^{-2}$ S cm$^{-1}$ under the conditions of a temperature of 35-80° C. and a relative humidity of 90%.

18. The polymer electrolyte membrane having electric conductivity according to claim 13, wherein said electric conductivity is proton conductivity of $10^{-4}$-$10^{-2}$ S cm$^{-1}$ under the conditions of a temperature of 35-80° C. and a relative humidity of 90%.

* * * * *